(12) United States Patent
Jiang et al.

(10) Patent No.: US 10,479,819 B2
(45) Date of Patent: Nov. 19, 2019

(54) OXYNTOMODULIN ANALOGUE

(71) Applicant: Xianxing Jiang, Guangzhou, Guangdong (CN)

(72) Inventors: Xianxing Jiang, Guangzhou (CN); Yuanwen Chen, Lanzhou (CN)

(73) Assignee: JIANG, XIANXING, Guangzhou, Guangdong (CN)

( * ) Notice: Subject to any disclaimer, the term of this patent is extended or adjusted under 35 U.S.C. 154(b) by 88 days.

(21) Appl. No.: 15/300,069

(22) PCT Filed: May 28, 2015

(86) PCT No.: PCT/CN2015/080042
§ 371 (c)(1),
(2) Date: Sep. 28, 2016

(87) PCT Pub. No.: WO2016/045400
PCT Pub. Date: Mar. 31, 2016

(65) Prior Publication Data
US 2017/0183383 A1    Jun. 29, 2017

(30) Foreign Application Priority Data

Sep. 23, 2014 (CN) .......................... 2014 1 0490280

(51) Int. Cl.
| | | |
|---|---|---|
| *C07K 14/00* | (2006.01) |
| *C07K 14/605* | (2006.01) |
| *A61K 8/64* | (2006.01) |
| *A61Q 19/06* | (2006.01) |
| *C07K 14/575* | (2006.01) |
| *A61K 47/54* | (2017.01) |
| *A61K 38/00* | (2006.01) |

(52) U.S. Cl.
CPC .............. *C07K 14/001* (2013.01); *A61K 8/64* (2013.01); *A61K 47/542* (2017.08); *A61Q 19/06* (2013.01); *C07K 14/575* (2013.01); *C07K 14/605* (2013.01); *A61K 38/00* (2013.01)

(58) Field of Classification Search
None
See application file for complete search history.

(56) References Cited

FOREIGN PATENT DOCUMENTS

| | | |
|---|---|---|
| CN | 101389648 | 3/2009 |
| CN | 103764673 | 4/2014 |
| JP | 2012511900 A | 5/2012 |
| NZ | 593811 A | 3/2013 |
| WO | WO-2006/134340 A3 | 12/2006 |
| WO | WO2010-070252 | * 6/2010 |
| WO | WO2010-096052 | * 8/2010 |
| WO | 2011006497 A1 | 1/2011 |
| WO | WO-2013/041678 A | 3/2013 |
| WO | WO2013-192129 | * 12/2013 |

OTHER PUBLICATIONS

Druce et al., "Investigation of Structure-Activity Relationships of Oxyntomodulin (Oxm) Using Oxm Analogs", Endocrinology, Apr. 2009, vol. 150 (4), pp. 1712-1721.
Maralayn R. Druce et al., "Investigation of Structure-Activity Relationships of Oxyntomodulin (Oxm) Using Oxm Anologs," Endocrinology, Apr. 2009, vol. 150, No. 4, pp. 1712-1722.

* cited by examiner

*Primary Examiner* — James H Alstrum-Acevedo
*Assistant Examiner* — Tara L Martinez
(74) *Attorney, Agent, or Firm* — Maschoff Brennan; Jonathan M. Benns

(57) ABSTRACT

Provided is an oxyntomodulin analogue. The analogue comprises GCGR and GLP-1R dual agonist activity, improved enzymolysis stability and biological activity, and no adverse reactions. The analogue can be used to prepare medication for treating hyperphagia, obesity and diabetes.

10 Claims, 3 Drawing Sheets
Specification includes a Sequence Listing.

OXYNTOMODULIN ANALOGUE

FIELD OF THE INVENTION

The present invention belongs to the field of biochemical technology, and relates to an oxyntomodulin analogue peptide.

The present invention also relates to therapeutic uses of the new oxyntomodulin analogue.

BACKGROUND OF THE INVENTION

Diabetes mellitus (DM) is a metabolic disease that is characterized by absolute or relative deficiency of insulin. Relative or absolute deficiency of insulin can lead to hyperglycemia, which further cause metabolism disorder of three major nutrients, and ultimately affect normal physiological functions of the patients and cause complications. The patients with diabetes worldwide is increasing day by day, among adults aged 20-79 years, the number of the patients with diabetes in 2013 has reached 382 million, and it is estimated to reach 439 million by 2030. Among them, the population with diabetes in China is the highest in the world, and is about 110 million at present and still growing fast. The rise in obesity drives an increase in diabetes, and approximately 90% of people with type II diabetes may be classified obese. There are 246 million people worldwide with diabetes, and by 2025 it is estimated that 380 million will have diabetes. Many have additional cardiovascular risk factors including high/aberrant LDL and triglycerides and low HDL. Diabetes cannot be cured at present, and the patient can only rely on drugs for life. Traditional anti-diabetic drugs have their shortcomings, and there is an urgent need to develop new anti-diabetic drugs.

Compared with small-molecule chemical drugs and macro-molecule protein drugs, peptide drugs have their own advantages: first, most of them are derived from endogenous peptides or other natural peptides, clear structure, and have clear structures and mechanisms of action; second, compared with general small-molecule drugs, they have higher activity, less dosage, less toxic side effects, with amino acids as the end product of metabolism (free of toxic side effects); third, compared with the foreign proteins, they have low immunogenicity, and can be chemically synthesized, and the product has high purity and controllability on quality; and fourth, polypeptide drugs are often able to avoid the gastrointestinal digestion and overcome the drawbacks that protein molecules are destroyed by digestive enzymes and thus cannot be orally administrated.

Glucagon-like peptide (GLP-1) belongs to the family of incretins, which is a polypeptide mainly secreted by intestinal mucosal L cells, and has two active forms: GLP-1-(7-37) and GLP-1-(7-36)-amide. GLP-1 play an antidiabetic role by combining with the specific receptor glucagon like peptide-1 receptor (GLP1R), the main physiological functions are: to improve islet βcell function, to promote the secretion of insulin, to reduce postprandial blood glucose and maintain blood glucose homeostasis, to increase insulin biosynthesis, to inhibit glucagon secretion, to inhibit gastrointestinal motility especially gastric emptying so as to increase satiety, to decrease appetite and control body weight. Compared with traditional antidiabetic drugs, the advantage of the GLP-I is to maintain glucose homeostasis and control body weight effectively. (Cardiovascular effects of glucagonlike peptide-1 agonists, Am J Cardiol. 2011; 108:33B-41B. Cardiovascular effects of the DPP-4 inhibitors, Diab Vasc Dis Res. 2012; 9:109-16. Incretin mimetics as a novel therapeutic option for hepatic steatosis, Liver Int. 2006; 26: 1015-7.). GLP-1 has a very short half-life, and is degraded by dipeptidyl-peptidase-IV (DPP_IV) or Neutral endopeptidase (NEP) 24.11 soon after being secreted. Therefore, GLP-1 cannot be directly used in the clinic, and there is a need to develop an enzymolysis-resistant GLP-1 receptor agonist.

However, clinical trials have demonstrated the shortcomings of GLP-1 receptor agonists are also obvious, mainly in the following aspects:

However, clinical trials have proved that GLP-1 receptor agonist also has very obvious shortcomings, mainly in the following aspects: first, the short half-life leads to intensive injection frequency, and brings inconvenience to the patients; second, pharmacokinetics and security are not clear, and it is unclear how the introduced foreign chemical groups are metabolized and excreted and how do they influence the human body, and thus further investigation is needed. The latest preclinical study show that compared to a pure GLP-1R agonist, balanced glucagon like peptide-1 receptor and glucagon receptor (GLP-1R/GCGR) dual target agonist exhibits a more effective, safer treatment effect on obese mice, and also improve the blood glucose control (A new glucagon and GLP-1 co-agonist eliminates obesity in rodents, Nat Chem Biol. 2009; 5:749-57.). Related to this is the study on oxyntomodulin (OXM). OXM is a short peptide hormone secreted by intestinal epithelial L-cells, which is composed of 37 amino acids, and is an endogenous precursor of glucagon. OXM is a balanced GLP-1R/GCGR dual target agonist, its potency on glucagon receptor is 2-fold lower than on GLP-1 receptor, and is lower than that of the natural glucagon and GLP-1 on their respective receptor. Although the biological activity of natural OXM is low, the clinical research shows that consecutive subcutaneous injection of natural OXM over a four-week period still can significantly reduce the patient's body weight and decrease food intake. (Subcutaneous oxyntomodulin reduces body weight in overweight and obese subjects: a double-blind, randomized, controlled trial, Diabetes. 2005; 54: 2390-5.) OXM has a very short half-life, which may be inactivated rapidly by dipeptidyl peptidase IV (DPP-IV) on cell surface, and has poor stability in vivo.

GLP-1R/GCGR co-agonist has been proved to significantly reduce body weight and fat content in high fat diet-induced obesity rats (DIO rat), which is superior to any pure GLP-1R agonist, and also improve the blood glucose control. These changes may be associated with reduction in food intake and substantial increase in energy consumption. Another report pointed out that a long-acting GLP-1R/GCGR dual target agonist having protease resistance, compared with the long-acting GLP-IR agonist having the same effect, can significantly reduce body weight, reduce triglycerides and resist hyperglycemia. In addition, the long-acting GLP-1R/GCGR dual target agonist may improve metabolic parameters, such as blood insulin, leptin and adiponectin (Unimolecular dual incretins maximize metabolic benefits in rodents, monkeys, and humans, Sci Transl Med. 2013; 5:209.).

In summary, the development of GLP-1R/GCGR dual target agonist is currently the main direction for development of polypeptide drugs for treating diabetes. In recent years, researchers have developed several potential OXM analogues for injecting once a day and once a week. Among them, the most widely used modifier is mono-methoxy polyethylene glycol (methoxypoly ethylene glycol, mPEG), by increasing the molecular exclusion volume of OXM, reducing renal filtration clearance rate of the drug molecule, thereby prolonging the mPEG-modified drug's plasma half-life, so as to achieve the goal of weekly injection. Although this method can significantly improve the half-life of polypeptide drugs, the biological activities of most of the proteins are decreased with different degrees. Even more dangerous is, mPEG is a molecule that cannot be metabolized in human body, the polypeptide protein drugs derived from it may lead to renal vacuolation (Short communication: renal tubular vacuolation in animals treated with polyethyleneglycol-conjugated proteins, *Toxicol Sci.* 1998; 42: 152-7; Safety assessment on polyethylene glycols (PEGs) and their derivatives as used in cosmetic products. *Toxicology,* 2005; 214:1-38.). The vast majority of drug molecules modified by mPEG is used for tumor treatment, thus the toxicity of PEG is often overlooked greatly. From the nature of chemical point of view, the biochemical and physiological properties of polypeptide drugs may be solved fundamentally only by optimizing the polypeptide sequence, which is the fact that is recognized by biochemists; and on this basis, various indicators such as activity and stability of polypeptide drugs may be further improved by biochemical means.

SUMMARY OF THE INVENTION

The object of the present invention is to provide an oxyntomodulin (OXM) analogue. The inventors have modified the oxyntomodulin molecule through a great deal of experimental studies, and the results show that such oxyntomodulin analogues have a longer half-life, have an insulinotropic activity, and have no adverse events, and can be used for the treatment of diseases such as diabetes.

Another object of the present invention is to provide therapeutic uses of such oxyntomodulin analogues. The new oxyntomodulin analogues may potentially be used as a new generation drug for treating diabetes, or used for lowering blood glucose, or used for reducing body weight.

The present invention is based on the improvement of the parent peptides of oxyntomodulin (OXM), glucagon-like peptide (GLP-1), Exenatide and Glucagon. The parent peptide of oxyntomodulin (OXM) is as follows (SEQ ID NO.25):

His-Ser-Gln-Gly-Thr-Phe-Thr-Ser-Asp-Tyr-Ser-Lys-

Tyr-Leu-Asp-Ser-Arg-Arg-Ala-Gln-Asp-Phe-Val-Gln-

Trp-Leu-Met-Asn-Thr-Lys-Arg-Asn-Lys-Asn-Asn-Ile-

Ala-OH

The sequence of glucagon-like peptide (GLP-1) is as follows (SEQ ID NO.26):

His-Ala-Glu-Gly-Thr-Phe-Thr-Ser-Asp-Val-Ser-Ser-

Tyr-Leu-Glu-Gly-Gln-Ala-Ala-Lys-Glu-Phe-Ile-Ala-

Trp-Leu-Val-Lys-Gly-Arg-Gly-OH

The sequence of Exenatide is as follows (SEQ ID NO.27):

His-Gly-Glu-Gly-Thr-Phe-Thr-Ser-Asp-Leu-Ser-Lys-

Gln-Met-Glu-Glu-Glu-Ala-Val-Arg-Leu-Phe-Ile-Glu-

-continued
Trp-Leu-Lys-Asn-Gly-Gly-Pro-Ser-Ser-Gly-Ala-Pro-

Pro-Pro-Ser-NH$_2$

The sequence of Glucagon is as follows (SEQ ID NO.28):

His-Ser-Gln-Gly-Thr-Phe-Thr-Ser-Asp-Tyr-Ser-Lys-

Tyr-Leu-Asp-Ser-Arg-Arg-Ala-Gln-Asp-Phe-Val-Gln-

Trp-Leu-Met-Asn-Thr-OH

The first aspect of the present invention is to provide an oxyntomodulin analogue, and the oxyntomodulin analogue comprises the parent peptide represented by the following amino acid sequence (SEQ ID NO: 29):

His-Xaa2-Gln-Gly-Thr-Phe-Thr-Ser-Asp-Xaa10-Ser-

Lys-Xaa13-Leu-Asp-Xaa16-Xaa17-Xaa18-Ala-Xaa20-

Xaa21-Phe-Xaa23-Xaa24-Trp-Leu-Xaa27-Xaa28-Xaa29-

Xaa30-Xaa31-Xaa32-Xaa33-Xaa34-Xaa35-Xaa36-Xaa37-

Xaa38-Xaa39-Xaa40-COR$_1$ wherein, R$_1$=—OH or —NH$_2$;
Xaa2=Aib, Ser or D-Ser;
Xaa10=Lys or Tyr;
Xaa13=Lys or Tyr;
Xaa16=Ser, Aib, Lys or Glu;
Xaa17=Lys or Arg;
Xaa18=Arg or Ala;
Xaa20=His, Gln or Lys;
Xaa21=Asp or Glu;
Xaa23=He, Leu or Val;
Xaa24=Glu or Gln;
Xaa27=Met, Leu or is absent;
Xaa28=Ser, Asn, Asp, Arg or is absent;
Xaa29=Ala, Gly, Thr or is absent;
Xaa30=Gly or is absent;
Xaa31=Gly or is absent;
Xaa32=Pro or is absent;
Xaa33=Ser or is absent;
Xaa34=Ser or is absent;
Xaa35=Gly or is absent;
Xaa36=Ala or is absent;
Xaa37=Pro or is absent;
Xaa38=Pro or is absent;
Xaa39=Pro or is absent;
Xaa40=Ser or is absent.

In the amino acid sequence, at least one of Xaa10, Xaa16, Xaa17 or Xaa20 is Lys, the side chain of said at least one Lys or the Lys at position 12 is attached to a lipophilic substituent in such a way that a carboxyl group of the lipophilic substituent forms an amide bond with an amino group of a bridging group, the bridging group is attached to the parent peptide by means of a carboxyl group of the amino acid residue of the bridging group which for iris an amide bond with a N-terminal residue of Lys of the parent peptide.

The bridging group is Glu, Asp, and/or (PEG)m, wherein m is an integer of 2-10; and the lipophilic substituent is an acyl group selected from $CH_3(CH_2)_nCO$— or $HOOC(CH_2)_nCO$—, wherein n is an integer of 10-24.

The preferred bridging group may be Glu-(PEG)$_m$ or Asp-(PEG)$_m$, or (PEG)$_m$, which is attached in the way as follows:

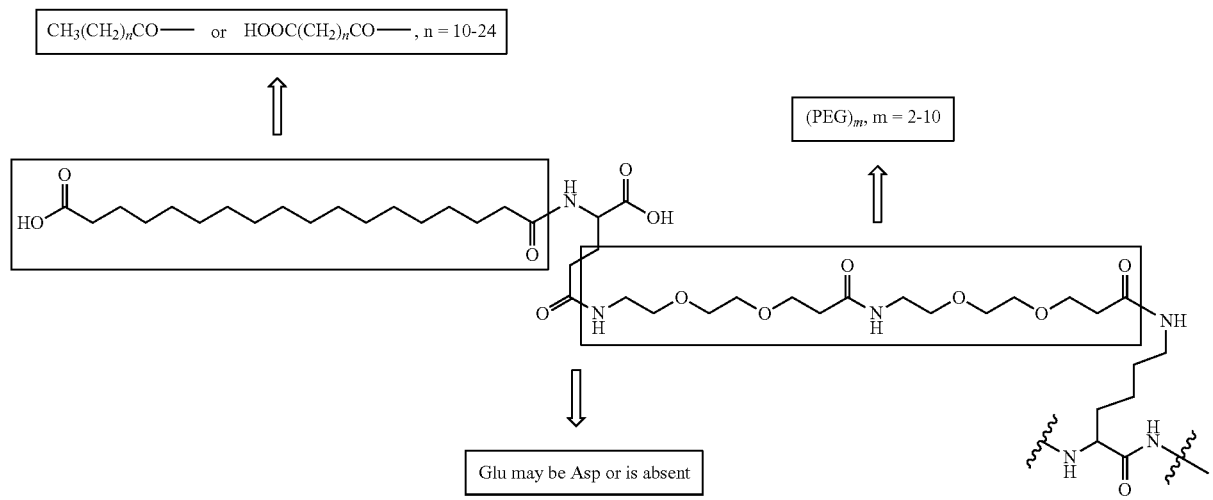

Preferred compounds of the present invention are parent peptides comprising the following amino acid sequence (SEQ ID NO: 29):

```
His-Xaa2-Gln-Gly-Thr-Phe-Thr-Ser-Asp-Xaa10-Ser-
Lys-Xaa13-Leu-Asp-Xaa16-Xaa17-Xaa18-Ala-Xaa20-
Xaa21-Phe-Xaa23-Xaa24-Trp-Leu-Xaa27-Xaa28-Xaa29-
Xaa30-Xaa31-Xaa32-Xaa33-Xaa34-Xaa35-Xaa36-Xaa37-
Xaa38-Xaa39-Xaa40-COR1
``` wherein, R1=—NH2;
Xaa2=Aib or D-Ser;
Xaa10=Lys or Tyr;
Xaa13=Lys or Tyr;
Xaa16=Ser, Aib, Glu or Lys;
Xaa17=Lys or Arg;
Xaa18=Arg or Ala;
Xaa20=His, Gln or Lys;
Xaa21=Asp or Glu;
Xaa23=He, Val;
Xaa24=Glu or Gln;
Xaa27=Met or Leu;
Xaa28=Asn, Arg, Asp or is absent;
Xaa29=Gly, Thr or is absent;
Xaa30=Gly or is absent;
Xaa31=Gly or is absent;
Xaa32=Pro or is absent;
Xaa33=Ser or is absent;
Xaa34=Ser or is absent;
Xaa35=Gly or is absent;
Xaa36=Ala or is absent;
Xaa37=Pro or is absent;
Xaa38=Pro or is absent;
Xaa39=Pro or is absent;
Xaa40=Ser or is absent.

More preferred compounds are compounds 1 to 24, which comprises the parent peptide having an amino acid sequence shown in SEQ ID NO.1 to 24.

Throughout the specification of this application, the conventional three letter codes for naturally occurring amino acids are used, as well as generally accepted three letter codes for other amino acids, such as Aib (aminoisobutyric acid), Orn (ornithine).

The compound of the present invention is based on the theory that the intramolecular bridges can stabilise the helical structure of the molecule and so increase potency and/or selectivity at the GLP-1R or GCGR receptors. The compounds of the invention may carry one or more intramolecular bridge within the sequence. Each such bridge is formed between the side chains of two amino acid residues which are typically separated by three amino acids in the linear sequence. For example, the bridge may be formed between the side chains of residue pairs 12 and 16, 16 and 20, 17 and 21, or 20 and 24. The two side chains can be linked to one another through ionic interactions, or by covalent bonds. Thus these pairs of residues may comprise oppositely charged side chains in order to form a salt bridge by ionic interactions. For example, one of the residues may be Glu or Asp, while the other residue may be Lys or Arg. The pairings of Lys and Glu and Lys and Asp, may also be capable of reacting to form a lactam ring.

The compound of the present invention is based on the theory that the lipophilic substituent can bind albumin in the blood stream, thus shielding the compounds of the invention from enzymatic degradation, which can increase the half-life of the compounds.

Another aspect of the present invention is to provide a pharmaceutical composition comprising the oxyntomodulin analogue. The pharmaceutical composition is prepared using the oxyntomodulin analogue as an active ingredient added with pharmaceutically acceptable carriers and/or excipients.

Another aspect of the invention is to provide medical use of the oxyntomodulin analogue of the present invention. Cell and animal experiments show that the oxyntomodulin analogue of the present invention has a hypoglycemic effect, can be used as a drug for the treatment of diabetes. The oxyntomodulin analogue of the present invention can also reduce body weight, and has potential use as a drug for the treatment of obesity.

The GLP-1R/GCGR dual target agonist mentioned in the present invention is a homologous polypeptide. The homologous polypeptide in the present invention refers to that the polypeptide originally has GLP-1, OXM, Glucagon or Exenatide amino acid sequence, but one or more amino acid residues have been conservatively substituted by different amino acid residues, and the resulting polypeptide can be used for implementing the present invention.

The polypeptides of the present invention can be used for preventing weight gain or promoting weight loss. The polypeptides may cause a decrease in food intake and/or increased energy expenditure, resulting in the observed effect on body weight. Independently of their effect on body weight, the compounds of the invention may have a beneficial effect on circulating cholesterol levels (being capable of lowering circulating LDL levels and increasing HDL/LDL ratio). Thus the polypeptides of the invention can be used for direct or indirect therapy of any condition caused or characterized by excess body weight, such as the treatment and/or prevention of obesity, morbid obesity, obesity linked inflammation, obesity linked gallbladder disease, obesity induced sleep apnea. The compounds of the present invention may also be used for the treatment of metabolic syndrome, hypertension, atherogenic dyslipidimia, atherosclerois, arteriosclerosis, coronary heart disease, or stroke. The effects of the polypeptides of the present invention in these conditions may be as a result of or associated with their effect on body weight, or may be independent thereof.

The person skilled in the art can appreciate that the pharmaceutical composition of the present invention is suitable for various administration routes, such as oral administration, percutaneous administration, intravenous administration, intramuscular administration, topical administration, intranasal drugs. According to the used administration route, the pharmaceutical composition of the present invention can be formulated into various suitable dosage forms, which comprises an effective amount of at least one polypeptide of the present invention and at least one pharmaceutically acceptable pharmaceutical carrier.

Examples of suitable dosage forms are tablets, capsules, sugar coated tablets, granules, oral liquid and syrup, ointment and paste for the skin surface, aerosol, nasal spray and sterile solution for injection.

The pharmaceutical composition comprising the polypeptide of the present invention may be prepared into solution or lyophilized powder for parenteral administration. Before use, an appropriate solvent or other pharmaceutically acceptable carrier can be added to reconfigurate the powder, and liquid formula is generally buffer, osmotic solution and aqueous solution.

The dosage of the polypeptide in the pharmaceutical composition of the present invention may vary in a wide range, which can be easily determined by the person skilled in this art according to certain factors such as the type of the disease, the severity of the disease, patient's body weight, the dosage form, the administration route.

The present invention has the advantages of:
1) having better biological activity compared with natural OXM with the same molecular,
2) showing a significant prolonged half-life and better stability in pharmacokinetics experiment of the drug,
3) high synthesis yield, good stability, easy to be produced on large scale, and low cost.

In particular embodiments, the following oxyntomodulin analogues are related, having the following sequences:

```
Compound 1 (SEQ ID NO. 1):
His-(D-Ser)-Gln-Gly-Thr-Phe-Thr-Ser-Asp-Tyr-Ser-Lys-Tyr-Leu-Asp-Ser-Lys(PEG₂-

PEG₂-Glu-CO(CH₂)₁₆CO₂H)-Ala-Ala-His-Asp-Phe-Val-Glu-Trp-Leu-Leu-Arg-

Ala-NH₂

Compound 2 (SEQ ID NO. 2):
His-(D-Ser)-Gln-Gly-Thr-Phe-Thr-Ser-Asp-Tyr-Ser-Lys-Tyr-Leu-Asp-Glu-Lys- Ala-Ala-Lys(PEG₂-PEG₂-Glu-CO(CH₂)₁₆CO₂H)-Glu-Phe-Ile-Glu-Trp-Leu-Leu-Arg- Ala-NH₂

Compound 3 (SEQ ID NO. 3):
His-(D-Ser)-Gln-Gly-Thr-Phe-Thr-Ser-Asp-Tyr-Ser-Lys-Tyr-Leu-Asp-Ser-Lys(PEG₂-

PEG₂-Glu-CO(CH₂)₁₆CO₂H)-Ala-Ala-His-Asp-Phe-Val-Glu-Trp-Leu-Leu-Asn-

Gly-Gly-Pro-Ser-Ser-Gly-Ala-Pro-Pro-Pro-Ser-NH₂

Compound 4 (SEQ ID NO. 4):
His-(D-Ser)-Gln-Gly-Thr-Phe-Thr-Ser-Asp-Tyr-Ser-Lys-Tyr-Leu-Asp-Glu-Lys- Ala-Ala-Lys(PEG₂-PEG₂-Glu-CO(CH₂)₁₆CO₂H)-Glu-Phe-Ile-Glu-Trp-Leu-Leu-Asn- Gly-Gly-Pro-Ser-Ser-Gly-Ala-Pro-Pro-Pro-Ser-NH₂

Compound 5 (SEQ ID NO. 5):
His-(D-Ser)-Gln-Gly-Thr-Phe-Thr-Ser-Asp-Lys(PEG₂-PEG₂-CO(CH₂)₁₄CH₃)-Ser- Lys-Tyr-Leu-Asp-Aib-Arg-Arg-Ala-Gln-Asp-Phe-Val-Gln-Trp-Leu-Met-Asn-Thr-Gly- Gly-Pro-Ser-Ser-Gly-Ala-Pro-Pro-Pro-Ser-NH₂

Compound 6 (SEQ ID NO. 6):
His-(D-Ser)-Gln-Gly-Thr-Phe-Thr-Ser-Asp-Lys(PEG₂-PEG₂-CO(CH₂)₁₆CO₂H)-

Ser-Lys-Tyr-Leu-Asp-Aib-Arg-Arg-Ala-Gln-Asp-Phe-Val-Gln-Trp-Leu-Met-Asn-Thr-

Gly-Gly-Pro-Ser-Ser-Gly-Ala-Pro-Pro-Pro-Ser-NH₂

Compound 7 (SEQ ID NO. 7):
His-(D-Ser)-Gln-Gly-Thr-Phe-Thr-Ser-Asp-Lys(PEG₂-PEG₂-Glu-CO(CH₂)₁₄CH₃)-
```

Ser-Lys-Tyr-Leu-Asp-Aib-Arg-Arg-Ala-Gln-Asp-Phe-Val-Gln-Trp-Leu-Met-Asn-

Thr-Gly-Gly-Pro-Ser-Ser-Gly-Ala-Pro-Pro-Pro-Ser-NH$_2$

Compound 8 (SEQ ID NO. 8):
His-(D-Ser)-Gln-Gly-Thr-Phe-Thr-Ser-Asp-Lys(PEG$_2$-PEG$_2$-Glu-CO(CH$_2$)$_{16}$CO$_2$H)-

Ser-Lys-Tyr-Leu-Asp-Aib-Arg-Arg-Ala-Gln-Asp-Phe-Val-Gln-Trp-Leu-Met-Asn-

Thr-Gly-Gly-Pro-Ser-Ser-Gly-Ala-Pro-Pro-Pro-Ser-NH$_2$

Compound 9 (SEQ ID NO. 9):
His-(D-Ser)-Gln-Gly-Thr-Phe-Thr-Ser-Asp-Tyr-Ser-Lys-Tyr-Leu-Asp-Lys(PEG$_2$-

PEG$_2$-CO(CH$_2$)$_{16}$CO$_2$H)-Arg-Arg-Ala-Gln-Asp-Phe-Val-Gln-Trp-Leu-Met-Asn-Thr-

Gly-Gly-Pro-Ser-Ser-Gly-Ala-Pro-Pro-Pro-Ser-NH$_2$

Compound 10 (SEQ ID NO. 10):
His-(D-Ser)-Gln-Gly-Thr-Phe-Thr-Ser-Asp-Tyr-Ser-Lys-Tyr-Leu-Asp-Lys(PEG$_2$-

PEG$_2$-Glu-CO(CH$_2$)$_{14}$CH$_3$)-Arg-Arg-Ala-Gln-Asp-Phe-Val-Gln-Trp-Leu-Met-Asn-Thr-

Gly-Gly-Pro-Ser-Ser-Gly-Ala-Pro-Pro-Pro-Ser-NH$_2$

Compound 11 (SEQ ID NO. 11):
His-(D-Ser)-Gln-Gly-Thr-Phe-Thr-Ser-Asp-Tyr-Ser-Lys-Tyr-Leu-Asp-Lys(PEG$_2$-

PEG$_2$-Glu-CO(CH$_2$)$_{16}$CO$_2$H)-Arg-Arg-Ala-Gln-Asp-Phe-Val-Gln-Trp-Leu-Met-Asn-

Thr-Gly-Gly-Pro-Ser-Ser-Gly-Ala-Pro-Pro-Pro-Ser-NH$_2$

Compound 12 (SEQ ID NO. 12):
His-(D-Ser)-Gln-Gly-Thr-Phe-Thr-Ser-Asp-Tyr-Ser-Lys-Tyr-Leu-Asp-Aib-Lys (PEG$_2$-PEG$_2$-CO(CH$_2$)$_{16}$CO$_2$H)-Arg-Ala-Gln-Asp-Phe-Val-Gln-Trp-Leu-Met-Asn-Thr- Gly-Gly-Pro-Ser-Ser-Gly-Ala-Pro-Pro-Pro-Ser-NH$_2$ Compound 13 (SEQ ID NO. 13):
His-(D-Ser)-Gln-Gly-Thr-Phe-Thr-Ser-Asp-Tyr-Ser-Lys-Tyr-Leu-Asp-Aib-Lys (PEG$_2$-PEG$_2$-Glu-CO(CH$_2$)$_{14}$CH$_3$)-Arg-Ala-Gln-Asp-Phe-Val-Gln-Trp-Leu-Met-Asn- Thr-Gly-Gly-Pro-Ser-Ser-Gly-Ala-Pro-Pro-Pro-Ser-NH$_2$ Compound 14 (SEQ ID NO. 14):
His-(D-Ser)-Gln-Gly-Thr-Phe-Thr-Ser-Asp-Tyr-Ser-Lys-Tyr-Leu-Asp-Aib-Lys (PEG$_2$-PEG$_2$-Glu-CO(CH$_2$)$_{16}$CO$_2$H)-Arg-Ala-Gln-Asp-Phe-Val-Gln-Trp-Leu-Met-Asn- Thr-Gly-Gly-Pro-Ser-Ser-Gly-Ala-Pro-Pro-Pro-Ser-NH$_2$ Compound 15 (SEQ ID NO. 15):
His-(D-Ser)-Gln-Gly-Thr-Phe-Thr-Ser-Asp-Tyr-Ser-Lys(PEG$_2$-PEG$_2$-CO(CH$_2$)$_{14}$CH$_3$)-

Lys-Leu-Asp-Aib-Arg-Arg-Ala-Gln-Asp-Phe-Val-Gln-Trp-Leu-Met-Asn-Thr-

Gly-Gly-Pro-Ser-Ser-Gly-Ala-Pro-Pro-Pro-Ser-NH$_2$

Compound 16 (SEQ ID NO. 16):
His-(D-Ser)-Gln-Gly-Thr-Phe-Thr-Ser-Asp-Tyr-Ser-Lys(PEG$_2$-PEG$_2$-CO(CH$_2$)$_{16}$CO$_2$H)-

Lys-Leu-Asp-Aib-Arg-Arg-Ala-Gln-Asp-Phe-Val-Gln-Trp-Leu-Met-Asn-Thr-

Gly-Gly-Pro-Ser-Ser-Gly-Ala-Pro-Pro-Pro-Ser-NH$_2$

Compound 17(SEQ ID NO. 17):
His-(D-Ser)-Gln-Gly-Thr-Phe-Thr-Ser-Asp-Tyr-Ser-Lys(PEG$_2$-PEG$_2$-Glu-CO(CH$_2$)$_{14}$CH$_3$)-

Lys-Leu-Asp-Aib-Arg-Arg-Ala-Gln-Asp-Phe-Val-Gln-Trp-Leu-Met-Asn-

Thr-Gly-Gly-Pro-Ser-Ser-Gly-Ala-Pro-Pro-Pro-Ser-NH$_2$

Compound 18 (SEQ ID NO. 18):
His-(D-Ser)-Gln-Gly-Thr-Phe-Thr-Ser-Asp-Tyr-Ser-Lys(PEG$_2$-PEG$_2$-Glu-CO(CH$_2$)$_{16}$CO$_2$H)-

Lys-Leu-Asp-Aib-Arg-Arg-Ala-Gln-Asp-Phe-Val-Gln-Trp-Leu-Met-Asn-

Thr-Gly-Gly-Pro-Ser-Ser-Gly-Ala-Pro-Pro-Pro-Ser-NH$_2$

-continued

Compound 19(SEQ ID NO. 19):
His-Aib-Gln-Gly-Thr-Phe-Thr-Ser-Asp-Lys(PEG$_2$-PEG$_2$-Glu-CO(CH$_2$)$_{14}$CH$_3$)-Ser- Lys-Tyr-Leu-Asp-Glu-Arg-Arg-Ala-Gln-Asp-Phe-Val-Gln-Trp-Leu-Leu-Asp-Gly- Gly-Pro-Ser-Ser-Gly-Ala-Pro-Pro-Pro-Ser-NH$_2$ Compound 20 (SEQ ID NO. 20):
His-Aib-Gln-Gly-Thr-Phe-Thr-Ser-Asp-Lys(PEG$_2$-PEG$_2$-Glu-CO(CH$_2$)$_{16}$CO$_2$H)-

Ser-Lys-Tyr-Leu-Asp-Glu-Arg-Arg-Ala-Gln-Asp-Phe-Val-Gln-Trp-Leu-Leu-Asp-Gly-

Gly-Pro-Ser-Ser-Gly-Ala-Pro-Pro-Pro-Ser-NH$_2$

Compound 21 (SEQ ID NO. 21):
His-Aib-Gln-Gly-Thr-Phe-Thr-Ser-Asp-Lys(PEG$_2$-PEG$_2$-Glu-CO(CH$_2$)$_{14}$CH$_3$)-Ser- Lys-Tyr-Leu-Asp-Aib-Arg-Arg-Ala-Gln-Asp-Phe-Val-Gln-Trp-Leu-Leu-Asp-Gly- Gly-Pro-Ser-Ser-Gly-Ala-Pro-Pro-Pro-Ser-NH$_2$ Compound 22 (SEQ ID NO. 22):
His-Aib-Gln-Gly-Thr-Phe-Thr-Ser-Asp-Lys(PEG$_2$-PEG$_2$-Glu-CO(CH$_2$)$_{16}$CO$_2$H)-

Ser-Lys-Tyr-Leu-Asp-Aib-Arg-Arg-Ala-Gln-Asp-Phe-Val-Gln-Trp-Leu-Leu-Asp-Gly-

Gly-Pro-Ser-Ser-Gly-Ala-Pro-Pro-Pro-Ser-NH$_2$

Compound 23 (SEQ ID NO. 23):
His-(D-Ser)-Gln-Gly-Thr-Phe-Thr-Ser-Asp-Tyr-Ser-Lys-Tyr-Leu-Asp-Glu-Lys- Ala-Ala-Lys(PEG$_2$-PEG$_2$-CO(CH$_2$)$_{14}$CH$_3$)-Glu-Phe-Ile-Glu-Trp-Leu-Leu-Asn-Gly-Gly- Pro-Ser-Ser-Gly-Ala-Pro-Pro-Pro-Ser-NH$_2$ Compound 24 (SEQ ID NO. 24):
His-(D-Ser)-Gln-Gly-Thr-Phe-Thr-Ser-Asp-Tyr-Ser-Lys-Tyr-Leu-Asp-Glu-Lys- Ala-Ala-Lys(PEG$_2$-PEG$_2$-Glu-CO(CH$_2$)$_{14}$CH$_3$)-Glu-Phe-Ile-Glu-Trp-Leu-Leu-Asn-Gly-
Gly-Pro-Ser-Ser-Gly-Ala-Pro-Pro-Pro-Ser-NH$_2$ In the above sequences, Lys modification may be one of the following structures:

Lys(PEG$_2$-PEG$_2$-γGlu-CO(CH$_2$)$_{14}$CH$_3$):

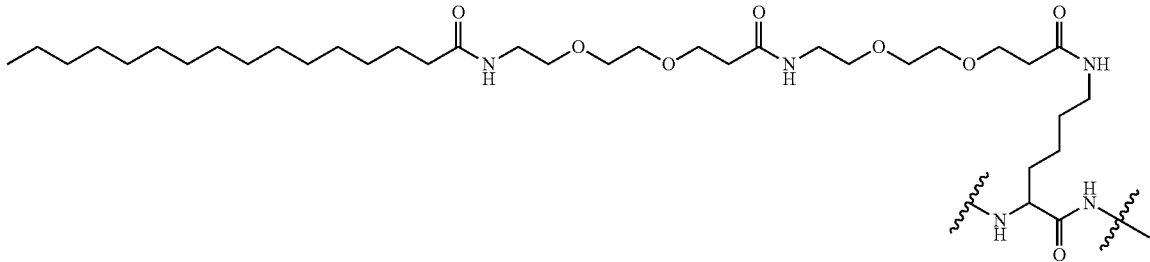

Lys(PEG$_2$-PEG$_2$-γGlu-CO(CH$_2$)$_{14}$CH$_3$):

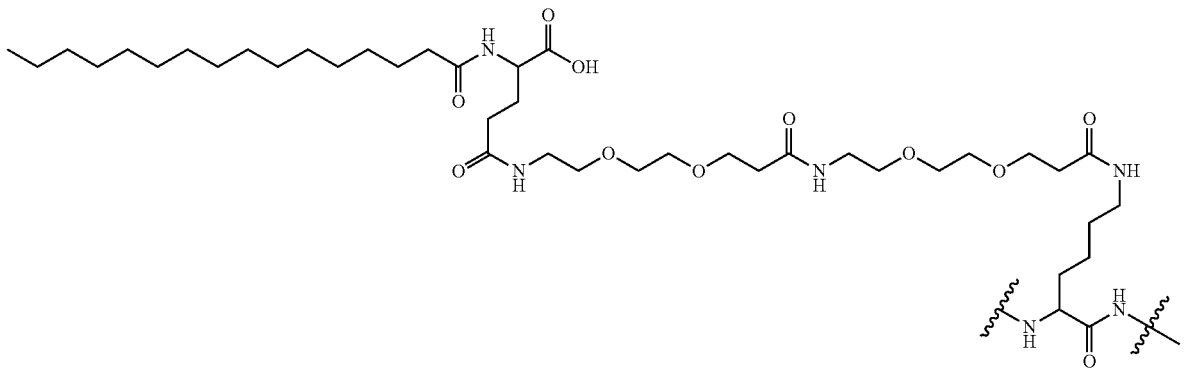

Lys(PEG$_2$-PEG$_2$-CO(CH$_2$)$_{16}$CO$_2$H):

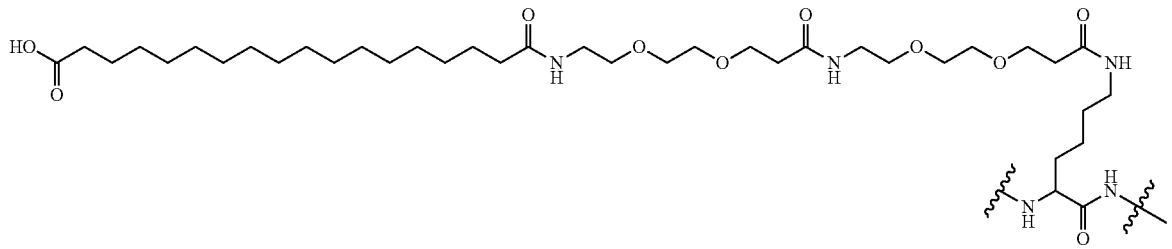

Lys(PEG$_2$-PEG$_2$-γGlu-CO(CH$_2$)$_{16}$CO$_2$H):

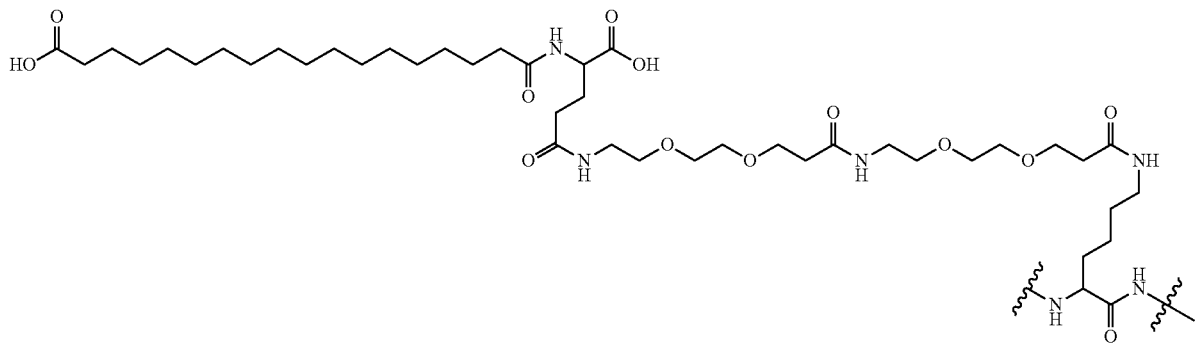

The above Lys attached to the lipophilic substituent may be replaced by:

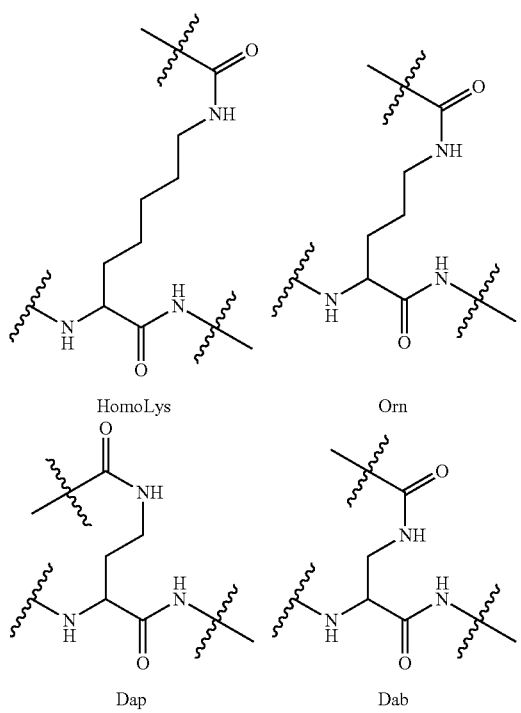

The abbreviations used in the present invention are defined as follows:

Boc is tert-butyloxycarbonyl, Fmoc is Dutch oxycarbonyl group, t-Bu is tert-butyl, ivDDe is 1-(4,4-dimethyl-2,6-dioxo-cyclohexylidene)-3-methyl-butyl removal and lipophilic substituent, resin is resin, TFA is trifluoroacetic acid, EDT is 1,2-ethanedithiol, Phenol is phenol, FBS is fetal bovine serum, BSA is bovine serum albumin, HPLC is high performance liquid chromatography, GLP-1R is glucagon-like peptide-1 receptor, GCGR is glucagon receptor, GLP-1 is glucagon-like peptide, mPEG is mono-methoxy-polyethylene diol, OXM is oxyntomodulin, His is histidine, Ser is serine, D-Ser is D-serine, Gln is glutamine, Gly is glycine, Glu is glutamic acid, Ala is alanine acid, Thr is threonine, Lys is lysine, Arg is arginine, Tyr is tyrosine, Asp i§ aspartic acid, Trp is tryptophan, Phe is phenylalanine, Ile is isoleucine, Leu is leucine, Cys is cysteine, Pro is proline, Val is valine, Met is methionine, Asn is asparagines, HomoLys is homolysine, Orn is ornithine, Dap is diaminopimelic acid, and Dab is 2,4-diaminobutyric acid.

DETAILED DESCRIPTION OF THE INVENTION

Figure 1:
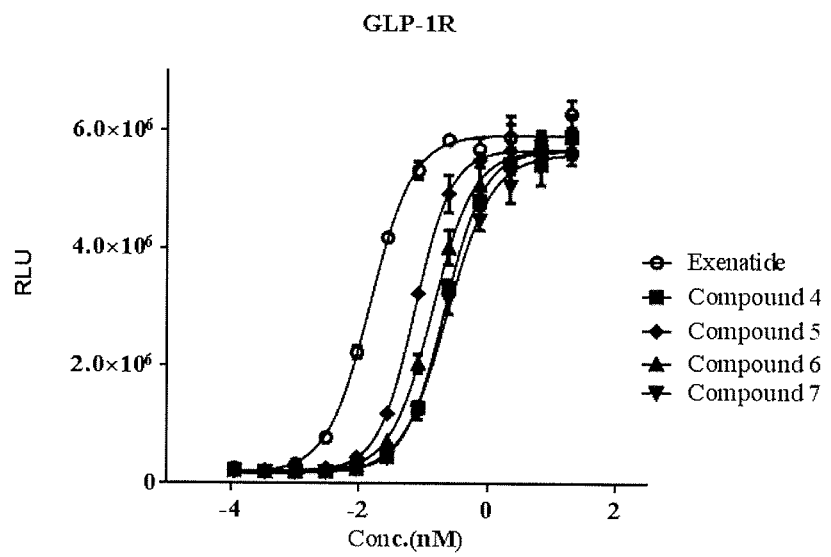
FIG. 1: stimulation curve of Exenatide and Compounds 4, 5, 6, 7 on GLP-IR.

The embodiments of the present invention will be described in detail hereafter in conjunction with the examples, but the person skilled in the art will appreciate that the following examples are only intended to illustrate the present invention and should not be construed to limit the scope of the present invention. Unless otherwise specified, the examples were carried out according to conventional conditions or the conditions recommended by manufacturers. The reagents or instruments used, the manufacture of which were not specified, were all conventional products can be obtained commercially.

Example 1 Synthesis of Octadecanedioic Acid Mono-Tert-Butyl Ester

Octadecanoic acid (31.4 g, 100 mmol) was suspended in toluene (250 ml), and the mixture was heated to reflux. N,N-dimethylformamide di-tert-butyl acetal (50.9 g, 250 mmol) was added dropwise over 4 hours. The mixture was refluxed overnight. The solvent was removed under vacuum, and at 50° C., the crude material was suspended in DCM/ethyl acetate (500 ml, 1:1) and stirred for 15 minutes. The solid was collected by filtration and triturated in DCM (200 mL), filtered and evaporated under vacuum to give 20 g of crude mono-tert-butyl-hexadecane, which was recrystallized in heptane (200 ml) to give 12.9 g of octadecanedioic acid mono-tert-butyl ester (33%). Except recrystallization, this mono-ester can be purified by chromatography on silica in AcOEt/heptane. $^1$H-NMR (400 MHz, $CDCl_3$) δ: 2.35 (t, 2H), 2.20 (t, 2H), 1.65-1.55 (m, 4H), 1.44 (s, 9H), 1.34-1.20 (m, 22H).

Example 2 Synthesis of Polypeptide Compound

Synthesis of polypeptide compound 1 and polypeptide compound 5 was taken as an example.

Materials:

All amino acids were purchased from NovaBiochem company. Unless otherwise specified, all reagents were analytical grade, purchased from Sigma company. Protein Technologies PRELUDE 6-channel polypeptide synthesizer. Phenomenex Luna C18 preparative column (46 mm×250 mm) was used for purification of the polypeptides. High performance liquid chromatography instrument was manufactured by Waters company. MS analysis was determined using Agilent mass spectrometer.

Method:

1. Synthesis of Polypeptide Compound 1

Structure Sequence:

His-(D-Ser)-Gln-Gly-Thr-Phe-Thr-Ser-Asp-Tyr-Ser-Lys-Tyr-Leu-Asp-Ser-Lys($PEG_2$-$PEG_2$-Glu-CO$(CH_2)_{16}CO_2H$)-Ala-Ala-His-Asp-Phe-Val-Glu-Trp-Leu-Leu-Arg-Ala-$NH_2$

1a) Main Peptide Chain Assembly:

The following polypeptide in a scale of 0.25 mol was synthesized on a CS336X peptide synthesizer (CS Bio American company) according to Fmoc/t-Bu strategy:

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Ser(OtBu)-Lys(ivDde)-Ala-Ala-His(Boc)-Asp(OtBu)-Phe-Val-Glu(OtBu)-Trp(Boc)-Leu-Leu-Arg(pbf)-Ala-rink amide resin (1) Step 1: 0.75 g of Rink amide resin was swelled in dichloromethane, and the resin was washed with N,N-dimethylformamide for three times;

(2) Step 2: The procedure reaction was performed using Rink amide resin as carrier, the mixture of benzotriazole-N,N,N',N'-tetramethyluronium hexafluorophosphate, 1-hydroxybenzotriazole and N,N-diisopropylethylamine at a molar ratio of 1:1:1 as coupling agent, and N, N-dimethylformamide as solvent, condensation reactions were performed to successively attach Fmoc-Arg(pbf)-OH, Fmoc-Leu-OH (2×), Fmoc-Trp(Boc)-OH, Fmoc-Glu(OtBu)-OH, Fmoc-Val-OH, Fmoc-Phe-OH, Fmoc-Asp(OtBu)-OH, Fmoc-His(Boc)-OH, Fmoc-Ala-OH (2×), Fmoc-Lys(ivDde)-OH, Fmoc-Ser(t-Bu)-OH, Fmoc-Asp(OtBu)-OH, Fmoc-Leu-OH, Fmoc-Tyr(t-Bu)-OH, Fmoc-Lys(Boc)-OH, Fmoc-Ser(t-Bu)-OH, Fmoc-Tyr(t-Bu)-OH, Fmoc-Asp(OtBu)-OH, Fmoc-Ser(t-Bu)-OH, Fmoc-Thr(t-Bu)-OH, Fmoc-Phe-OH, Fmoc-Thr(t-Bu)-OH, Fmoc-Gly-OH, Fmoc-Gln(OtBu)-OH, Fmoc-D-Ser(t-Bu)-OH and Boc-His(Boc)-OH to obtain Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Ser(OtBu)-Lys(ivDde)-Ala-Ala-His(Boc)-Asp(OtBu)-Phe-Val-Glu(OtBu)-Trp(Boc)-Leu-Leu-Arg(pbf)-Ala-rink amide resin, wherein in each condensation reaction, the feeding amount of Fmoc-protected amino acid and the amount of the resin was at a molar ratio of 1:1~6:1; in each condensation reaction, the amount of benzotriazole-N,N,N',N'-tetramethyluronium hexafluorophosphate and the amount of Fmoc protected amino acid was at a molar ratio of 3:1.

1b) Removal of 1-(4,4-dimethyl-2,6-dioxo-cyclohexylidene)-3-methyl-butyl (ivDde) and Introduction of Lipophilic Substituent In the solution of N-methylpyrrolidone:dichloromethane=1:1 (volume ratio), the protected peptidyl resin synthesized in 1a) was washed twice, and freshly prepared 2.0% hydrazine hydrate N-methylpyrrolidone solution was added. The reaction mixture was shaken at room temperature for 12.0 minutes, and then filtered. The hydrazine treatment step was repeated twice to obtain:

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Ser(OtBu)-Lys-Ala-Ala-His(Boc)-Asp(OtBu)-Phe-Val-Glu(OtBu)-Trp(Boc)-Leu-Leu-Arg(pbf)-Ala-rink amide resin. Subsequently, the resin was thoroughly washed with dichloromethane and N-methylpyrrolidon. Thereto was added a mixed coupling solution of FmocNH-$PEG_2$-OH, benzotriazole-N,N,N',N'-tetramethyluronium hexafluorophosphate, 1-hydroxybenzotriazole and diisopropylethylamine in N-methylpyrrolidon, shaken for 3.0 hours, filtrated and washed. The hydrazine treatment was repeated twice to obtain:

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Ser(OtBu)-Lys(Fmoc-$PEG_2$-OH)-Ala-Ala-His(Boc)-Asp(OtBu)-Phe-Val-Glu(OtBu)-Trp(Boc)-Leu-Leu-Arg(pbf)-Ala-rink amide resin. The Fmoc group was removed in piperidine/N, N-dimethylformamide solution, Fmoc-$PEG_2$-OH coupling reaction was repeated once to obtain:

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Ser(OtBu)-Lys(Fmoc-$PEG_2$-$PEG_2$-OH)-Ala-Ala-His(Boc)-Asp(OtBu)-Phe-Val-Glu(OtBu)-Trp(Boc)-Leu-Leu-Arg(pbf)-Ala-rink amide resin. The Fmoc group was removed in piperidine/N,N-dimethylformamide solution, then according to the conventional conditions, coupling of Fmoc-Glu-OtBu, tBu mono-protected stearidonic fatty acid was performed sequentially to obtain:

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Ser(OtBu)-Lys(Fmoc-$PEG_2$-$PEG_2$-Glu-CO$(CH_2)_{16}CO_2tBu$)-Ala-Ala-His(Boc)-Asp(OtBu)-Phe-Val-Glu(OtBu)-Trp(Boc)-Leu-Leu-Arg(pbf)-Ala-rink amide resin.

1c) Removal of Polypeptide Full Protection:

Boc-His(Boc)-D-Ser(t-Bu)-Gln(OtBu)-Gly-Thr(t-Bu)-Phe-Thr(t-Bu)-Ser(tBu)-A sp(OtBu)-Tyr(t-Bu)-Ser(t-Bu)-Lys(Boc)-Tyr(t-Bu)-Leu-Asp(OtBu)-Ser(OtBu)-Lys(Fmoc-PEG$_2$-PEG$_2$-Glu-CO(CH$_2$)$_{16}$CO$_2$tBu)-Ala-Ala-His(Boc)-Asp(OtBu)-Phe-Val-Glu(OtBu)-Trp(Boc)-Leu-Leu-Arg(pbf)-Ala-rink amide resin was added to a round bottom flask, under ice bath, added with a cutting fluid of TFA/EDT/Phenol/H$_2$O (88/2/5/5, volume ratio), heated, controlling the temperature of the lysates at 25° C., and reacted for 120 minutes. After filtration, the filter cake was washed with a small amount of trifluoroacetic acid for three times, and the filtrate was combined. The filtrate was slowly poured into ice diethyl ether with stirring, placed on standing for at least 1.0 hours to precipitate completely. The supernatant was removed, and the precipitate was centrifuged and washed with ice diethyl ether for six times to give crude compound: His-(D-Ser)-Gln-Gly-Thr-Phe-Thr-Ser-Asp-Tyr-Ser-Lys-Tyr-Leu-Asp-Ser-Lys(PEG$_2$-PEG$_2$-Glu-CO(CH$_2$)$_{16}$CO$_2$H)-Ala-Ala-His-Asp-Phe-Val-Glu-Trp-Leu-Leu-Arg-Ala-NH$_2$.

d) Purification of Polypeptide Compound:

The crude product obtained in 1c was dissolved with 5.0% acetic acid solution in acetonitrile: H$_2$O=1:1 (volume ratio), and purified twice by semipreparative HPLC on a 5.0 m reverse-phase C18-packed 50 mm×250 mm column. The column was eluted with 30-60% acetonitrile −0.1% trifluoroacetic acid/H$_2$O gradient at 40 mL/min for 45.0 minutes, and the fractions containing the peptide were collected, and concentrated to remove acetonitrile, and then lyophilized, to obtain pure product with HPLC purity greater than 95%. The isolated product was analyzed by LC-MS, and the m/z value of protonated molecular ion peak was found to be: 4116.0, and the theoretical value is 4116.6.

2. Synthesis of polypeptide Compound 5

Structure Sequence:

His-(D-Ser)-Gln-Gly-Thr-Phe-Thr-Ser-Asp-Lys(PEG$_2$-PEG$_2$-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$

2a) Main Peptide Chain Assembly:

The following polypeptide in a scale of 0.25 mol was synthesized on a CS336X peptide synthesizer (CS Bio American company) according to Fmoc/t-Bu strategy Boc-His(Boc)-D-Ser(t-Bu)-Gln(OtBu)-Gly-Thr(t-Bu)-Phe-Thr(t-Bu)-Ser(tBu)-Asp(OtBu)-Lys(ivDde)-Ser(t-Bu)-Lys(Boc)-Tyr(t-Bu)-Leu-Asp(OtBu)-Aib-Arg(Pbf)-Arg(Pbf)-Ala-Gln(Trt)-Asp(OtBu)-Phe-Val-Gln(Trt)-Trp(Boc)-Leu-Met-Asn(Trt)-Thr(t-Bu)-Gly-Gly-Pro-Ser(t-Bu)-Ser(t-Bu)-Gly-Ala- Pro-Pro-Pro-Ser(t-Bu)-rink amide resin (1) Step 1: 0.75 g of Rink amide MBHA-LL resin (Novabiochem, loading 0.34 mmol/g) was swelled in dichloromethane (DCM) for 1 hour, and the resin was fully washed with N, N-dimethylformamide (DMF) for three times;

(2) Step 2: The procedure reaction was performed using Rink amide resin as carrier, the mixture of 6-chloro-benzotriazole-1,1,3,3-tetramethyluronium hexafluorophosphate (HCTU), organic base N,N-diisopropylethylamine (DIEPA) at a molar ratio of 1:1 as coupling agent, and N, N-dimethylformamide (DMF) as solvent, the condensation reactions were performed to successively link Fmoc-Ser(t-Bu)-OH, Fmoc-Pro-OH (3×), Fmoc-Ala-OH, Fmoc-Gly-OH, Fmoc-Ser(t-Bu)-OH (2×), Fmoc-Pro-OH, Fmoc-Gly-OH (2×), Fmoc-Thr(t-Bu)-OH, Fmoc-Asn(Trt)-OH, Fmoc-Met-OH, Fmoc-Leu-OH, Fmoc-Trp(Boc)-OH, Fmoc-Glu(OtBu)-OH, Fmoc-Val-OH, Fmoc-Phe-OH, Fmoc-Asp(OtBu)-OH, Fmoc-Gln(Trt)-OH, Fmoc-Ala-OH, Fmoc-Arg(Pbf)-OH (2×), Fmoc-Aib-OH, Fmoc-Asp(OtBu)-OH, Fmoc-Leu-OH, Fmoc-Tyr(t-Bu)-OH, Fmoc-Lys(Boc)-OH, Fmoc-Ser(t-Bu)-OH, Fmoc-Lys(ivDde)-OH, Fmoc-Asp(OtBu)-OH, Fmoc-Ser(t-Bu)-OH, Fmoc-Thr(t-Bu)-OH, Fmoc-Phe-OH, Thr(t-Bu)-OH, Fmoc-Gly-OH, Fmoc-Gln(Trt)-OH, Fmoc-D-Ser(t-Bu)-OH, Boc-His(Boc)-OH to obtain Boc-His(Boc)-D-Ser(t-Bu)-Gln(OtBu)-Gly-Thr(t-Bu)-Phe-Thr(t-Bu)-Ser(tBu)-Asp(OtBu)-Lys(ivDde)-Ser(t-Bu)-Lys(Boc)-Tyr(t-Bu)-Leu-Asp(OtBu)-Aib-Arg(Pbf)-Arg(Pbf)-Ala-Gln(Trt)-Asp(OtBu)-Phe-Val-Gln(Trt)-Trp(Boc)-Leu-Met-Asn(Trt)-Thr(t-Bu)-Gly-Gly-Pro-Ser(t-Bu)-Ser(t-Bu)-Gly-Ala- Pro-Pro-Pro-Ser(t-Bu)-rink amide resin. Subsequently, the resin was thoroughly washed with N, N-dimethylformamide (DMF), dichloromethane (DCM), methanol, dichloromethane (DCM), N, N-dimethylformamide (DMF) for three times respectively.

It should be noted that: 1) wherein the feeding amount of the first amino acid FFmoc-Ser(t-Bu)-OH and the amount of the resin was at a molar ratio of 1:1~6:1; 2) in each of the subsequent condensation reactions, each of the amount of Fmoc protected amino acid, 6-chloro-benzotriazole-1,1,3,3-tetramethyluronium hexafluorophosphate (HCTU), organic base N, N-diisopropylethylamine (DIEPA) was excess by 2-8 times, the reaction time was 1-5 hours.

2b) Removal of 1-(4,4-dimethyl-2,6-dioxo-cyclohexylidene)-3-methyl-butyl (ivDde) and Introduction of Lipophilic Substituent The resin was washed twice in the solution of N,N-dimethylformamide (DMF)/dichloromethane (DCM)=1:1 (volume ratio), and added with freshly prepared 3.0% hydrazine hydrate in N, N-dimethylformamide (DMF). The reaction mixture was shaken at room temperature for 10~30 minutes, and then filtered. The hydrazine treatment step was repeated five times to obtain:

Boc-His(Boc)-D-Ser(t-Bu)-Gln(OtBu)-Gly-Thr(t-Bu)-Phe-Thr(t-Bu)-Ser(tBu)-Asp(OtBu)-Lys-Ser(t-Bu)-Lys(Boc)-Tyr(t-Bu)-Leu-Asp(OtBu)-Aib-Arg(Pbf)-Arg(Pbf)-Ala-Gln(Trt)-Asp(OtBu)-Phe-Val-Gln(Trt)-Trp(Boc)-Leu-Met-Asn(Trt)-Thr(t-Bu)-Gly-Gly-Pro-Ser(t-Bu)-Ser(t-Bu)-Gly-Ala-Pro- Pro-Pro-Ser(t-Bu)-rink amide resin. Subsequently, the resin was thoroughly washed with N, N-dimethylformamide (DMF), dichloromethane (DCM), methanol (Methanol), dichloromethane (DCM), N, N-dimethylformamide (DMF) for three times respectively.

Thereto was added a mixed coupling solution of FmocNH-PEG$_2$-OH (Quanta BioDesign), 2-(7-azo BTA)-N,N,N',N'-tetramethyluronium hexafluorophosphate (HATU), diisopropylethyl amine (DIEPA) of N, N-dimethylformamide (DMF) (5 times excess of each), shaken for 2 hours, and filtrated. Subsequently, the resin was thoroughly washed with N, N-dimethylformamide (DMF), dichloromethane (DCM), methanol, dichloromethane (DCM), N,N-dimethylformamide (DMF) for three times respectively to obtain: Boc-His(Boc)-D-Ser(t-Bu)-Gln(OtBu)-Gly-Thr(t-Bu)-Phe-Thr(t-Bu)-Ser(tBu)-Asp(OtBu)-Lys(Fmoc-PEG$_2$)-Ser(t-Bu)-Lys(Boc)-Tyr(t-Bu)-Leu-Asp(OtBu)-Aib-Arg(Pbf)-Arg(Pbf)-Ala-Gln(Trt)-Asp(OtBu)-Phe-Val-Gln(Trt)-Trp(Boc)-Leu-Met-Asn(Trt)-Thr(t-Bu)-Gly-Gly-Pro-Ser(t-Bu)-Ser(t-Bu)-Gly-Ala-Pro-Pro-Pro-Ser(t-Bu)-rink amide resin. Subsequently, the resin was thoroughly washed with N,N-dimethylformamide (DMF), dichloromethane (DCM), methanol, dichloromethane (DCM), N,N-dimethylformamide (DMF) for three times respectively.

20% Piperidine/N, N-dimethylformamide (DMF) solution was used to remove the Fmoc group (30 minutes, repeated removal for twice). Thereto is added a mixed coupling solution of Fmoc-PEG-OH, 2-(7-azo BTA)-N,N,N',N'-tetramethyluronium hexafluorophosphate (HATU), diisopropylethyl amine (DIEPA) in N, N-dimethylformamide (DMF) was added (5 times excess of each). The coupling reaction produced:

Boc-His(Boc)-D-Ser(t-Bu)-Gln(OtBu)-Gly-Thr(t-Bu)-Phe-Thr(t-Bu)-Ser(tBu)-Asp(OtBu)-Lys(Fmoc-PEG$_2$-PEG$_2$)-Ser(t-Bu)-Lys(Boc)-Tyr(t-Bu)-Leu-Asp(OtBu)-Aib-Arg (Pbf)-Arg(Pbf)-Ala-Gln(Trt)-Asp(OtBu)-Phe-Val-Gln(Trt)-Trp(Boc)-Leu-Met-Asn(Trt)-Thr(t-Bu)-Gly-Gly-Pro-Ser(t-Bu)-Ser(t-Bu)-Gly-Ala-Pro-Pro-Pro-Ser(t-Bu)-rink amide resin. Subsequently, the resin was thoroughly washed with N, N-dimethylformamide (DMF), dichloromethane (DCM), methanol (Methanol), dichloromethane (DCM), N, N-dimethylformamide (DMF) for three times respectively.

20% Piperidine/N, N-dimethylformamide (DMF) solution was used to remove the Fmoc group (30 minutes, repeated removal for twice). Mixed coupling solution of hexadecanoic acid (palmitic acid), 2-(7-azo BTA)-N,N,N', N'-tetramethyluronium hexafluorophosphate (HATU), diisopropylethyl amine (DIEPA) of N,N-dimethylformamide (DMF) was added (5-fold excess of each). The coupling reaction produced:

Boc-His(Boc)-D-Ser(t-Bu)-Gln(OtBu)-Gly-Thr(t-Bu)-Phe-Thr(t-Bu)-Ser(tBu)-Asp(OtBu)-Lys(PEG$_2$-PEG$_2$-C16)-Ser(t-Bu)-Lys(Boc)-Tyr(t-Bu)-Leu-Asp(OtBu)-Aib-Arg(Pbf)-Arg(Pbf)-Ala-Gln(Trt)-Asp(OtBu)-Phe-Val-Gln(Trt)-Trp(Boc)-Leu-Met-Asn(Trt)-Thr(t-Bu)-Gly-Gly-Pro-Ser(t-Bu)-Ser(t-Bu)-Gly-Ala-Pro-Pro-Pro-Ser(t-Bu)-rink amide resin. Subsequently, the resin was thoroughly washed with N,N-dimethylformamide (DMF), dichloromethane (DCM), methanol, dichloromethane (DCM) for three times respectively, and dried under vacuum.

2c) Removal of Polypeptides Full Protection:

Boc-His(Boc)-D-Ser(t-Bu)-Gln(OtBu)-Gly-Thr(t-Bu)-Phe-Thr(t-Bu)-Ser(tBu)-Asp(OtBu)-Lys(PEG$_2$-PEG$_2$-C16)-Ser(t-Bu)-Lys(Boc)-Tyr(t-Bu)-Leu-Asp(OtBu)-Aib-Arg(Pbf)-Arg(Pbf)-Ala-Gln(Trt)-Asp(OtBu)-Phe-Val-Gln(Trt)-Trp(Boc)-Leu-Met-Asn(Trt)-Thr(t-Bu)-Gly-Gly-Pro-Ser(t-Bu)-Ser(t-Bu)-Gly-Ala-Pro-Pro-Pro-Ser(t-Bu)-rink amide resin was added with a cutting fluid TFA/Phenol/thioanisole/EDT/H2O (82.5:5:5:2.5:5, volume ratio), heated, controlling the temperature of the lysates at 25° C., and reacted for 2.5 hours. After filtration, the filter cake was washed with a small amount of trifluoroacetic acid for three times, and the filtrate was combined. The filtrate was slowly poured into ice diethyl ether with stirring, placed on standing for more than 2 hours to precipitate completely. The precipitate was centrifuged and washed with ice diethyl ether for three times to give crude compound:

His-(D-Ser)-Gln-Gly-Thr-Phe-Thr-Ser-Asp-Lys(PEG$_2$-PEG$_2$-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$

2d) Purification of Polypeptide Compound:

The crude product obtained in 2c was dissolved in a solution of acetonitrile (ACN): H$_2$O=1:1 (volume ratio), and purified by preparative HPLC on a 5.0 m reverse-phase C18-packed 46 mm×250 mm column. The column was subjected to gradient elution, with 30% acetonitrile (containing 0.05% trifluoroacetic acid)/H$_2$O (containing 0.05% trifluoroacetic acid) as a starting, adding the proportion of acetonitrile at a rate of 1.33%/min, at a flow rate of 40 mL/min, for 30 min. The reactions containing the peptide were collected, and lyophilized to obtain pure product with HPLC purity greater than 95% (if the purity does not meet the requirements, HPLC purification can be repeated once). The isolated product was analyzed by LC-MS.

Based on the above synthetic steps, the polypeptide compounds synthesized the present invention comprises (Table 1):

TABLE 1

Structure of polypeptide compounds synthesized in the examples of the present invention

| Polypeptide (SEQ ID NO.) | Sequence | Theoretical Mass | Observed Mass |
|---|---|---|---|
| 1 | His-(D-Ser)-Gln-Gly-Thr-Phe-Thr-Ser-Asp-Tyr-Ser-Lys-Tyr-Leu-Asp-Ser-Lys(PEG$_2$-PEG$_2$-Glu-CO(CH$_2$)$_{16}$CO$_2$H)-Ala-Ala-His-Asp-Phe-Val-Glu-Trp-Leu-Leu-Arg-Ala-NH$_2$ | 4114.1 | 4116.0 |
| 2 | His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-Glu-CO(CH$_2$)$_{16}$CO$_2$H)-Glu-Phe-Ile-Glu-Trp-Leu-Leu-Arg-Ala-NH$_2$ | 4175.2 | 4176.9 |
| 3 | His-(D-Ser)-Gln-Gly-Thr-Phe-Thr-Ser-Asp-Tyr-Ser-Lys-Tyr-Leu-Asp-Ser-Lys(PEG$_2$-PEG$_2$-Glu-CO(CH$_2$)$_{16}$CO$_2$H)-Ala-Ala-His-Asp-Phe-Val-Glu-Trp-Leu-Leu-Asn-Gly-Gly-Pro-Ser-Ser-Gly-Ala-Pro-Pro-Pro-Ser-NH$_2$ | 4892.4 | 4894.8 |
| 4 | His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-Glu-CO(CH$_2$)$_{16}$CO$_2$H)-Glu-Phe-Ile-Glu-Trp-Leu-Leu-Asn-Gly-Gly-Pro-Ser-Ser-Gly-Ala-Pro-Pro-Pro-Ser-NH$_2$ | 4953.5 | 4955.1 |
| 5 | His-(D-Ser)-Gln-Gly-Thr-Phe-Thr-Ser-Asp-Lys(PEG$_2$-PEG$_2$-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 4890.5 | 4891.5 |
| 6 | His-(D-Ser)-Gln-Gly-Thr-Phe-Thr-Ser-Asp-Lys(PEG$_2$-PEG$_2$-CO(CH$_2$)$_{16}$CO$_2$H)-Ser-Lys-Tyr-Leu-Asp- | 4948.5 | 4949.6 |

TABLE 1-continued

Structure of polypeptide compounds synthesized in the examples of the present invention

| Polypeptide (SEQ ID NO.) | Sequence | Theoretical Mass | Observed Mass |
|---|---|---|---|
|  | Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ |  |  |
| 7 | His-(D-Ser)-Gln-Gly-Thr-Phe-Thr-Ser-Asp-Lys(PEG$_2$-PEG$_2$-Glu-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5019.5 | 5020.6 |
| 8 | His-(D-Ser)-Gln-Gly-Thr-Phe-Thr-Ser-Asp-Lys(PEG$_2$-PEG$_2$-Glu-CO(CH$_2$)$_{16}$CO$_2$H)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5077.6 | 5078.5 |
| 9 | His-(D-Ser)-Gln-Gly-Thr-Phe-Thr-Ser-Asp-Tyr-Ser-Lys-Tyr-Leu-Asp-Lys(PEG$_2$-PEG$_2$-CO(CH$_2$)$_{16}$CO$_2$H)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5026.5 | 5027.6 |
| 10 | His-(D-Ser)-Gln-Gly-Thr-Phe-Thr-Ser-Asp-Tyr-Ser-Lys-Tyr-Leu-Asp-Lys(PEG$_2$-PEG$_2$-Glu-CO(CH$_2$)$_{14}$CH$_3$)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5097.6 | 5098.4 |
| 11 | His-(D-Ser)-Gln-Gly-Thr-Phe-Thr-Ser-Asp-Tyr-Ser-Lys-Tyr-Leu-Asp-Lys(PEG$_2$-PEG$_2$-Glu-CO(CH$_2$)$_{16}$CO$_2$H)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5155.6 | 5156.8 |
| 12 | His-(D-Ser)-Gln-Gly-Thr-Phe-Thr-Ser-Asp-Tyr-Ser-Lys-Tyr-Leu-Asp-Aib-Lys(PEG$_2$-PEG$_2$-CO(CH$_2$)$_{16}$CO$_2$H)-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 4955.5 | 4956.6 |
| 13 | His-(D-Ser)-Gln-Gly-Thr-Phe-Thr-Ser-Asp-Tyr-Ser-Lys-Tyr-Leu-Asp-Aib-Lys(PEG$_2$-PEG$_2$-Glu-CO(CH$_2$)$_{14}$CH$_3$)-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5026.5 | 5027.6 |
| 14 | His-(D-Ser)-Gln-Gly-Thr-Phe-Thr-Ser-Asp-Tyr-Ser-Lys-Tyr-Leu-Asp-Aib-Lys(PEG$_2$-PEG$_2$-Glu-CO(CH$_2$)$_{16}$CO$_2$H)-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5084.5 | 5085.6 |
| 15 | His-(D-Ser)-Gln-Gly-Thr-Phe-Thr-Ser-Asp-Tyr-Ser-Lys(PEG$_2$-PEG$_2$-CO(CH$_2$)$_{14}$CH$_3$)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 4890.5 | 4891.6 |
| 16 | His-(D-Ser)-Gln-Gly-Thr-Phe-Thr-Ser-Asp-Tyr-Ser-Lys(PEG$_2$-PEG$_2$-CO(CH$_2$)$_{16}$CO$_2$H)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 4948.5 | 4949.6 |
| 17 | His-(D-Ser)-Gln-Gly-Thr-Phe-Thr-Ser-Asp-Tyr-Ser-Lys(PEG$_2$-PEG$_2$-Glu-CO(CH$_2$)$_{14}$CH$_3$)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5019.5 | 5020.6 |
| 18 | His-(D-Ser)-Gln-Gly-Thr-Phe-Thr-Ser-Asp-Tyr-Ser-Lys(PEG$_2$-PEG$_2$-Glu-CO(CH$_2$)$_{16}$CO$_2$H)-Lys-Leu-Asp-Aib-Arg-Arg-Ala-Gln-Asp-Phe-Val-Gln-Trp- | 5077.6 | 5078.3 |

TABLE 1-continued

Structure of polypeptide compounds synthesized in the examples of the present invention

| Polypeptide (SEQ ID NO.) | Sequence | Theoretical Mass | Observed Mass |
|---|---|---|---|
| | Leu-Met-Asn-Thr-Gly-Gly-Pro-Ser-Ser-Gly-Ala-Pro-Pro-Pro-Ser-$NH_2$ | | |
| 19 | His-Aib-Gln-Gly-Thr-Phe-Thr-Ser-Asp-Lys($PEG_2$-$PEG_2$-Glu-CO($CH_2$)$_{14}CH_3$)-Ser-Lys-Tyr-Leu-Asp-Glu-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-$NH_2$ | 4945.5 | 4946.9 |
| 20 | His-Aib-Gln-Gly-Thr-Phe-Thr-Ser-Asp-Lys($PEG_2$-$PEG_2$-Glu-CO($CH_2$)$_{16}CO_2H$)-Ser-Lys-Tyr-Leu-Asp-Glu-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-$NH_2$ | 5002.6 | 5003.8 |
| 21 | His-Aib-Gln-Gly-Thr-Phe-Thr-Ser-Asp-Lys($PEG_2$-$PEG_2$-Glu-CO($CH_2$)$_{14}CH_3$)-Ser-Lys-Tyr-Leu-Asp-Aib-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-$NH_2$ | 4901.8 | 4903.3 |
| 22 | His-Aib-Gln-Gly-Thr-Phe-Thr-Ser-Asp-Lys($PEG_2$-$PEG_2$-Glu-CO($CH_2$)$_{16}CO_2H$)-Ser-Lys-Tyr-Leu-Asp-Aib-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-$NH_2$ | 4958.9 | 4960.3 |
| 23 | His-(D-Ser)-Gln-Gly-Thr-Phe-Thr-Ser-Asp-Tyr-Ser-Lys-Tyr-Leu-Asp-Glu-Lys-Ala-Ala-Lys($PEG_2$-$PEG_2$-CO($CH_2$)$_{14}CH_3$)-Glu-Phe-Ile-Glu-Trp-Leu-Leu-Asn-Gly-Gly-Pro-Ser-Ser-Gly-Ala-Pro-Pro-Pro-Ser-$NH_2$ | 4769.2 | 4770.3 |
| 24 | His-(D-Ser)-Gln-Gly-Thr-Phe-Thr-Ser-Asp-Tyr-Ser-Lys-Tyr-Leu-Asp-Glu-Lys-Ala-Ala-Lys($PEG_2$-$PEG_2$-Glu-CO($CH_2$)$_{14}CH_3$)-Glu-Phe-Ile-Glu-Trp-Leu-Leu-Asn-Gly-Gly-Pro-Ser-Ser-Gly-Ala-Pro-Pro-Pro-Ser-$NH_2$ | 4897.5 | 4898.6 |

Example 3. In Vitro Activity Determination of GCGR and GLP-IR

Stimulation effect on glucagon-like peptide 1 receptor (GLP-1 receptor) and glucagon receptor was determined using cAMP assay kit manufactured by the Cisbo company, meanwhile the dose-effect curves of positive control compound glucagon like peptide 1 (GLP-1), Exenatide and Glucagon were detected.

5000 of HEK-293 cells, which are used in CRE-luciferase system and express human GCGR or GLP-1R stably, were inoculated into 384 well plates according to 98 L DMEM/10% FBS media/well. On the second day of inoculation, 2 L of sample to be tested was gradient transferred, and the cells were mixed and incubated for 12 hours. Before the cells are added to obtain dose-response curve ($EC_{50}$ values were determined from the curve), usually the compound to be tested was prepared into 10 diluted solutions containing from 0.005 nm to 100.0 nM, and Exenatide standard (purchased from Hangzhou Paitai Biochemical Technology Co., Ltd., purity >98%, Exenatide aceteate, CAS No.: 141732-76-5) was prepared into 10 standard solutions of 0.005 nm to 100.0 nm, and Glucagon standard (purchased from Sigma-Aldrich company, product No. and specifications: 1294036-2X2.94MG, CAS No.: 16941-32-5) was prepared into 10 standard solutions of 0.01 nm to 100 nm. After incubation, 10.0 L of luciferase reagent was added directly to each plate and mixed gently for 2 minutes. The plates were placed into an Elmer Perkin plate reader for reading. Concentration curve of the compound was made by drawing software Prism 5, and the $EC_{50}$ value was calculated.

Compared with oxyntomodulin purchased from Shanghai Yinggong Industrial Co., Ltd., product No.: Es-1240), the compounds of the present invention have higher relative GLP-1R selectivity and have higher potency on glucagon receptor and GLP-1 receptor.

TABLE 2

Average $EC_{50}$ values of the representative polypeptide compounds of the present invention

| Compound | GLP-1R ($EC_{50}$, nM) | GCGR ($EC_{50}$, nM) | GLP-1R/GCGR |
|---|---|---|---|
| Exenatide | 0.02 | >100 | <0.0004 |
| Glucagon | 3.1 | 0.032 | 1000 |
| Oxyntomodulin | 2.5 | 6.2 | 0.4 |
| 1 | 0.23 | 0.54 | 0.4 |
| 2 | 0.39 | 2.8 | 0.1 |
| 3 | 0.59 | 1.02 | 0.6 |
| 4 | 0.13 | 0.39 | 0.3 |
| 5 | 0.06 | 0.43 | 0.1 |
| 6 | 0.10 | 0.33 | 0.3 |
| 7 | 0.14 | 0.34 | 0.4 |
| 8 | 0.20 | 0.18 | 1.1 |
| 9 | 0.52 | 0.18 | 2.9 |

TABLE 2-continued

Average EC$_{50}$ values of the representative polypeptide
compounds of the present invention

| Compound | GLP-1R (EC$_{50}$, nM) | GCGR (EC$_{50}$, nM) | GLP-1R/GCGR |
|---|---|---|---|
| 10 | 0.35 | 0.11 | 3.3 |
| 11 | 0.15 | 0.18 | 0.8 |
| 12 | 0.32 | 0.15 | 2.1 |
| 13 | 0.44 | 0.16 | 2.8 |
| 14 | 0.40 | 0.19 | 2.1 |
| 15 | 1.5 | 0.6 | 2.5 |
| 16 | 0.60 | 0.2 | 3 |
| 17 | 0.68 | 0.58 | 1.2 |
| 18 | 0.76 | 0.18 | 4.2 |
| 19 | 0.14 | 0.56 | 0.25 |
| 20 | 0.09 | 0.48 | 0.18 |
| 21 | 0.15 | 0.66 | 0.23 |
| 22 | 0.06 | 0.32 | 0.19 |
| 23 | 0.13 | 0.43 | 0.30 |
| 24 | 0.16 | 0.58 | 0.28 |

Figure 2:
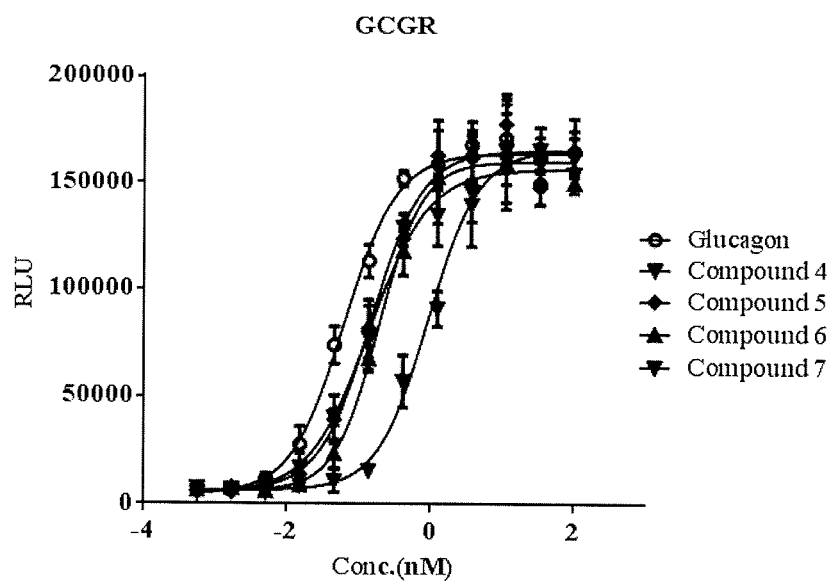
FIG. 2: stimulation curve of Glucagon and Compounds 4, 5, 6, 7 on GCGR.

FIG. 1: stimulation curve of Exenatide and Compounds 4, 5, 6, 7 on GLP-IR;

FIG. 2: stimulation curve of Glucagon and Compounds 4, 5, 6, 7 on GCGR;

Example 4 Pharmacokinetic Analysis of Compounds 4, 5, 6, 7, 19, 20, 21, 22, 23, 24 and Ex-4

Male CD1 mice (Nanjing University model animal research center) were respectively administrated by intravenous (IV) or subcutaneous injection (SC) with Compound 4, 5, 6, 7, 19, 20, 21, 22, 23 and 24 prepared according to the above examples and commercially available Exenatide pure product (Ex-4). Within 0-24 hours after administration the animals were bled at different times, and the plasma of each sample was collected and analyzed by LC-MS/MS determination method. Pharmacokinetic parameters of the drugs were calculated by methods of model dependence (for data obtained from IV) and model independence (data obtained from SC). By IV administration route, the elimination half-life of the compounds 4, 5, 6, 7, 19, 20, 21, 22, 23, and 24 was approximately 4-6 hours, and peak time ($T_{max}$) was about 12 hours, and the elimination half-life of Ex-4 was about 0.5 hours. By SC administration route, the peak time of the compounds 4, 5, 6, 7, 19, 20, 21, 22, 23 and 24 was about more than 12 hours, and the elimination half-life of Ex-4 was about 2 hours. The administration of compounds 4, 5, 6, 7, 19, 20, 21, 22, 23 and 24 by IV or SC route showed no clinical adverse effect.

Figure 3:
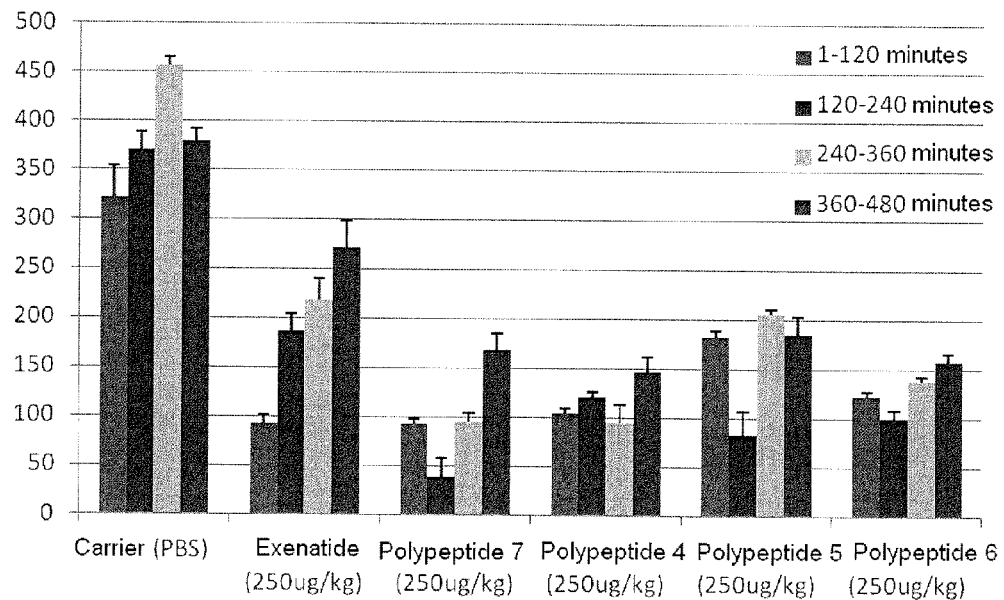
FIG. 3: Effect of Exenatide (Ex-4), Compounds 4, 5, 6 and 7 on insulin release after oral administration of glucose in male C57B1/6J mice; compared with the control group, $p<0.05$.
Figure 4:
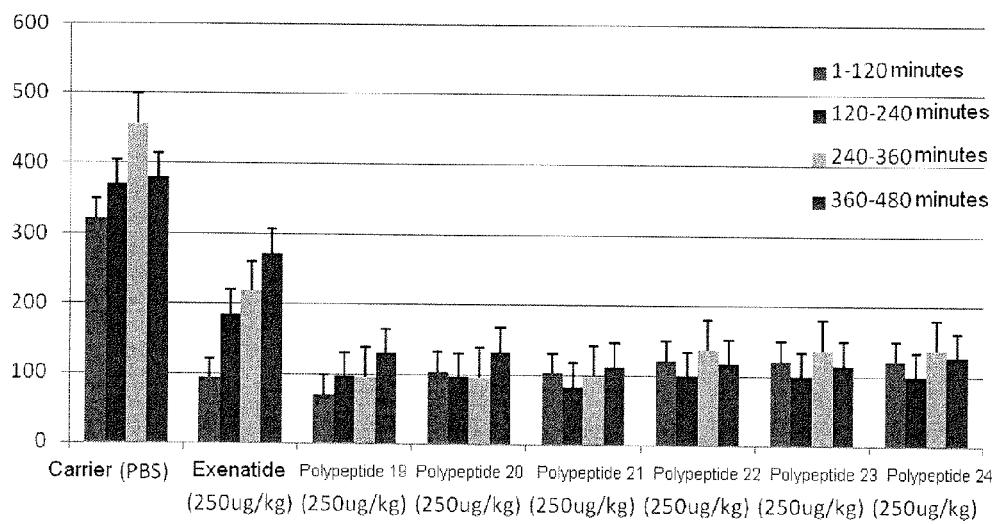
FIG. 4: Effect of Exenatide (Ex-4), Compounds 19, 20, 21, 22, 23 and 24 on insulin release after oral administration of glucose in male C57B1/6J mice; compared with the control group, $p<0.05$.

Example 5 Effect of Compounds 4, 5, 6, 7, 19, 20, 21, 22, 23, 24 and Ex-4 on Oral Glucose Tolerance 12-16 week-old male C57B1/6J mice (Nanjing University model animal research center) were randomly divided into groups 8 in each group, according to similar blood glucose (assessed by the blood samples obtained from the tail tip). After fasting (for 6 hours), the animals were administrated, and about 4 hours later, initial blood samples (fasting blood glucose level) were taken. Subsequently, the animals were administrated with an oral dose of glucose, and then put back into their cages (t=0). Blood glucose was measured at t=15 minutes, t=30 minutes, t=60 minutes, t=90 minutes and t=120 minutes. And then the animals were administrated with an oral dose of glucose again, and blood glucose was tracked until 8 hours. Polypeptides 4, 5, 6, 7, 19, 20, 21, 22, 23 and 24 (the dose of each compound was 250 µg/kg) significantly reduced the oral glucose tolerance. The software GraphPadPrism was used to process data to make the blood glucose change line chart and calculate the area under the curve to get the AUC diagram (FIGS. 3 and 4).

Compared with the carrier (PBS), the AUC of Exenatide (250 µg/kg) in the first OGTT curve period (1-120 min) was significantly reduced (P<0.05), but in the next three OGTT curve periods (120-480 min), the AUC was close to that of the control group (P>0.05). Compared with the carrier (PBS), the AUC of polypeptide 4, polypeptide 5, polypeptide 6, polypeptide 7, polypeptide 19, polypeptide 20, polypeptide 21, polypeptide 22, polypeptide 23 and polypeptide 24 was significantly decreased in all four OGTT curve periods (0-480 min) (P<0.05), the experimental results suggest that polypeptide 4, polypeptide 5, polypeptide 6, polypeptide 7, polypeptide 19, polypeptide 20, polypeptide 21, polypeptide 22, polypeptide 23 and polypeptide 24 have long-lasting hypoglycemic effect.

Figure 5:
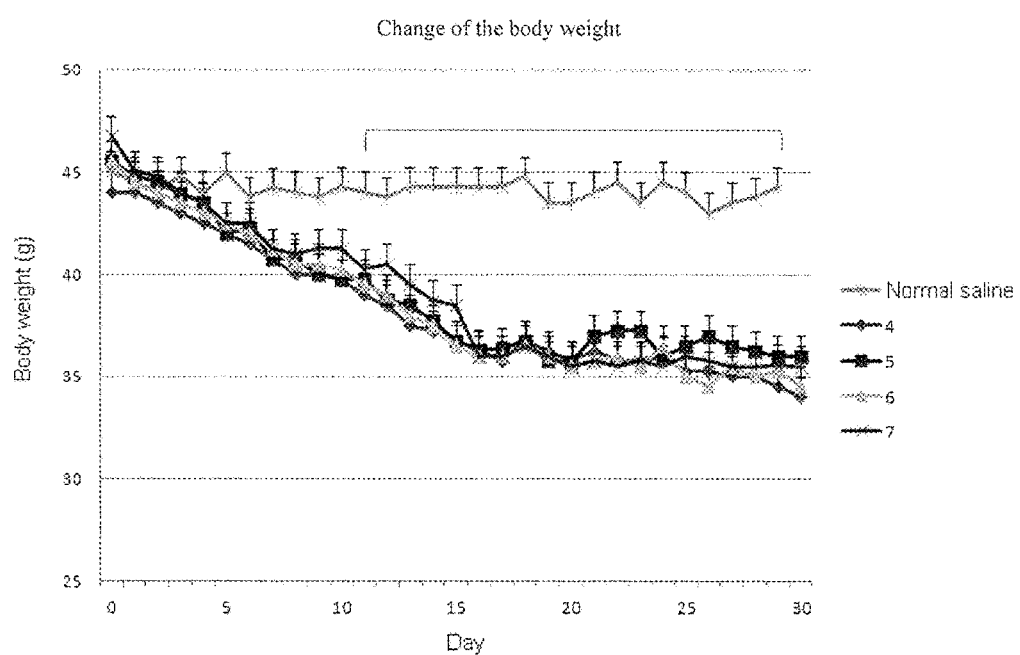
FIG. 5: Effect of polypeptide Compounds 4, 5, 6 and 7 on body weight in obese mice, compared with the control group, $p<0.05$.

Example 6 Effect of Compounds 5, 6, 7 on Body Weight in Obese Mice, Body Weight Reduction Research Forty 25-week-old DIO mice (Nanjing University model animal research center) were randomly divided into five groups (compound 4, 5, 6, 7, and normal saline group), 8 in each group, having no difference in the basis weight of each group. The mice group was respectively injected subcutaneously daily with compound 4 (250 µg/kg), compound 5 (250 µg/kg), compound 6 (250 µg/kg), compound 7 (250 µg/kg) and normal saline and then weighed. Compared with the normal saline group, during day 11 to day 30, the body weight in the compound 4, 5, 6, 7 groups were significantly lower than that of the normal saline group (P<0.05), having weight loss of about 20% (FIG. 5).

INDUSTRIAL APPLICATION

The OXM analogues of the present invention show GCGR and GLP-1R dual agonist activity, long half-life, and have high enzymolysis stability, high biological activity, and no adverse reactions. The compounds of the present invention can be synthesized with high yield, have good stability, are can be easily produced on a large scale with low cost, and can be used to prepare medication for treating hyperphagia, obesity and overweight, high cholesterol and diabetes.

Above detailed description of the invention does not limit the present invention, various changes and modifications may be made by the person skilled in this art in accordance with the present invention, without departing from the spirit and scope of the present invention, and are within the scope of the appended claims of the present invention.

What is claimed is:

1. An oxyntomodulin analogue, comprising a parent peptide having the following amino acid sequence (SEQ ID NO: 29):

His-Xaa2-Gln-Gly-Thr-Phe-Thr-Ser-Asp-Xaa10-Ser-

Lys-Xaa13-Leu-Asp-Xaa16-Xaa17-Xaa18-Ala-Xaa20-

Xaa21-Phe-Xaa23-Xaa24-Trp-Leu-Xaa27-Xaa28-Xaa29-

Xaa30-Xaa31-Xaa32-Xaa33-Xaa34-Xaa35-Xaa36-Xaa37-

Xaa38-Xaa39-Xaa40-COR$_1$ wherein, R$_1$=—OH or —NH$_2$;
Xaa2=Aib, Ser or D-Ser;
Xaa10=Lys or Tyr;
Xaa13=Lys or Tyr;
Xaa16=Ser, Aib, Lys;
Xaa17=Lys or Arg;
Xaa18=Arg or Ala;
Xaa20=His, Gln or Lys;
Xaa21=Asp or Glu;
Xaa23=Ile, Leu or Val;
Xaa24=Glu or Gln;
Xaa27=Met or Leu;
Xaa28=Ser, Asn, Asp, or Arg;
Xaa29=Ala, Gly, or Thr;
Xaa30=Gly;
Xaa31=Gly;
Xaa32=Pro;
Xaa33=Ser;
Xaa34=Ser;
Xaa35=Gly;
Xaa36=Ala;
Xaa37=Pro;
Xaa38=Pro;
Xaa39=Pro; and
Xaa40=Ser;
in the amino acid sequence of the parent peptide, at least one of Xaa10, Xaa16, Xaa17 or Xaa20 is Lys, the side chain of said at least one Lys or the Lys at position 12 is attached to a lipophilic substituent in such a way that a carboxyl group of the lipophilic substituent forms an amide bond with an amino group of a bridging group, the bridging group is attached to the parent peptide by means of a carboxy group of the amino acid residue of the bridging group which forms an amide bond with the amino group of the side chain of said at least one Lys or the Lys of the parent peptide;
the bridging group is Glu-(PEG)$_m$ or Asp-(PEG)$_m$ or (PEG)$_m$, wherein m is an integer of 2-10; and the lipophilic substituent is an acyl group selected from CH$_3$(CH$_2$)$_n$CO— or HOOC(CH2)$_n$CO—, wherein n is an integer of 10-24.

2. The oxyntomodulin analogue according to claim 1, wherein the parent peptide has an amino acid sequence of (SEQ ID NO: 29):

His-Xaa2-Gln-Gly-Thr-Phe-Thr-Ser-Asp-Xaa10-Ser-

Lys-Xaa13-Leu-Asp-Xaa16-Xaa17-Xaa18-Ala-Xaa20-

Xaa21-Phe-Xaa23-Xaa24-Trp-Leu-Xaa27-Xaa28-Xaa29-

Xaa30-Xaa31-Xaa32-Xaa33-Xaa34-Xaa35-Xaa36-Xaa37-

Xaa38-Xaa39-Xaa40-COR$_1$ wherein, R$_1$=—NH$_2$;
Xaa2=Aib or D-Ser;
Xaa10=Lys or Tyr;
Xaa13=Lys or Tyr;
Xaa16=Ser, Aib, or Lys;
Xaa17=Lys or Arg;
Xaa18=Arg or Ala;
Xaa20=His, Gln or Lys;
Xaa21=Asp or Glu;
Xaa23=Ile or Val;
Xaa24=Glu or Gln;
Xaa27=Met or Leu;
Xaa28=Asn, Arg, or Asp;
Xaa29=Gly or Thr;
Xaa30=Gly;
Xaa31=Gly;
Xaa32=Pro;
Xaa33=Ser;
Xaa34=Ser;
Xaa35=Gly;
Xaa36=Ala;
Xaa37=Pro;
Xaa38=Pro;
Xaa39=Pro; and
Xaa40=Ser.

3. The oxyntomodulin analogue according to claim 1, wherein that a molecular bridge is formed between the side chains of amino acid residue pairs 12 and 16, 16 and 20, 17 and 21, or 20 and 24.

4. The oxyntomodulin analogue according to claim 2, wherein the amino acid sequence of the parent peptide is a sequence selected from the group consisting of SEQ ID NO.7, SEQ ID NO.10, SEQ ID NO.13, and SEQ ID NO.17.

5. The oxyntomodulin analogue according to claim 1, wherein that-when the position 10, 12, 16, 17, or 20 of the amino acid sequence is Lys, the lipophilic substituent attached to the side chain of Lys is one of the following structures:

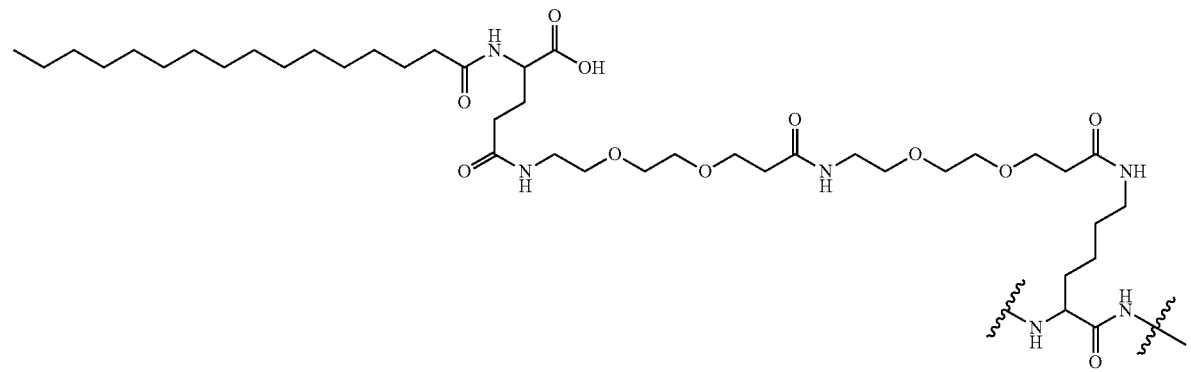

-continued

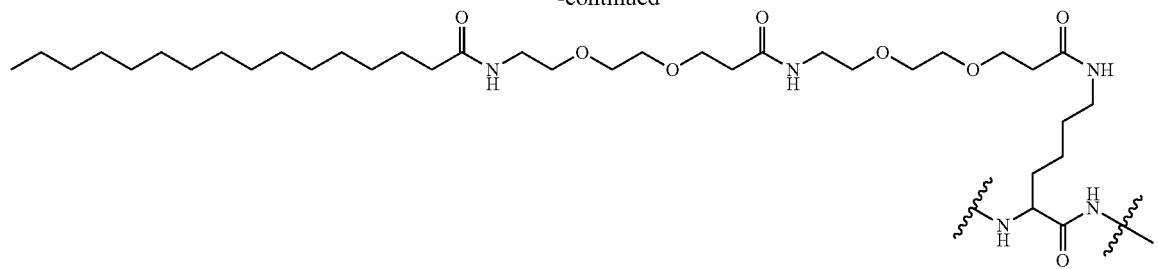

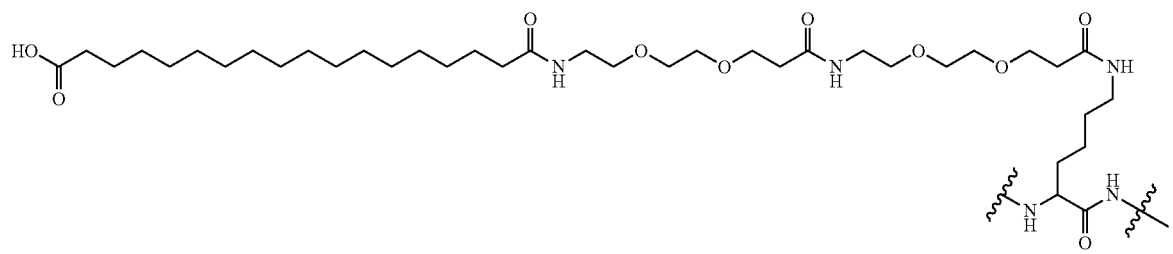

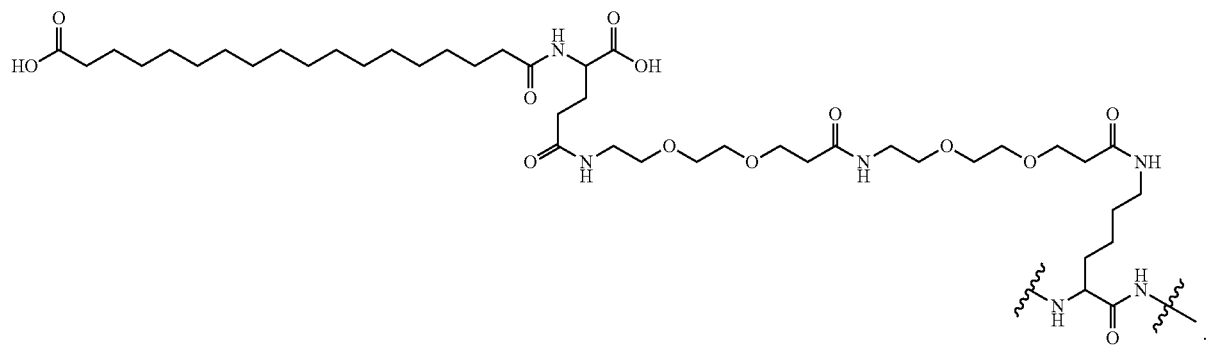

6. A pharmaceutical composition comprising the oxyntomodulin analogue of claim 1.

7. A method of making a drug for treating diabetes, the method comprising preparing the oxyntomodulin analogue of claim 1.

8. A method of making a drug for reducing blood glucose, the method comprising preparing the oxyntomodulin analogue of claim 1.

9. The oxyntomodulin analogue according to claim 3, wherein, when the position 16 of the amino acid sequence is Lys, the lipophilic substituent attached to the side chain of Lys is one of the following structures:

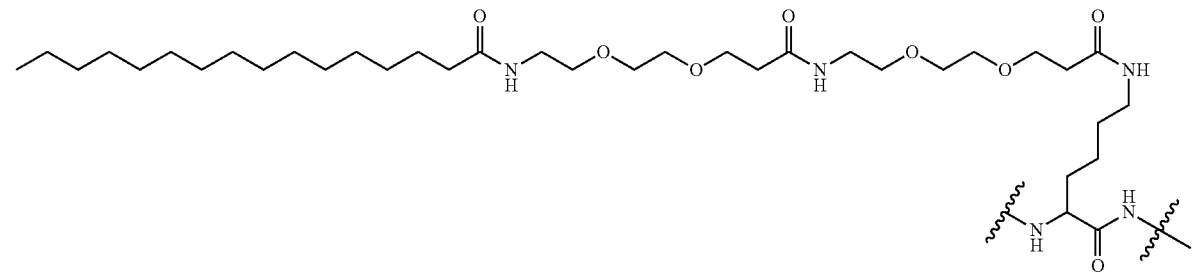

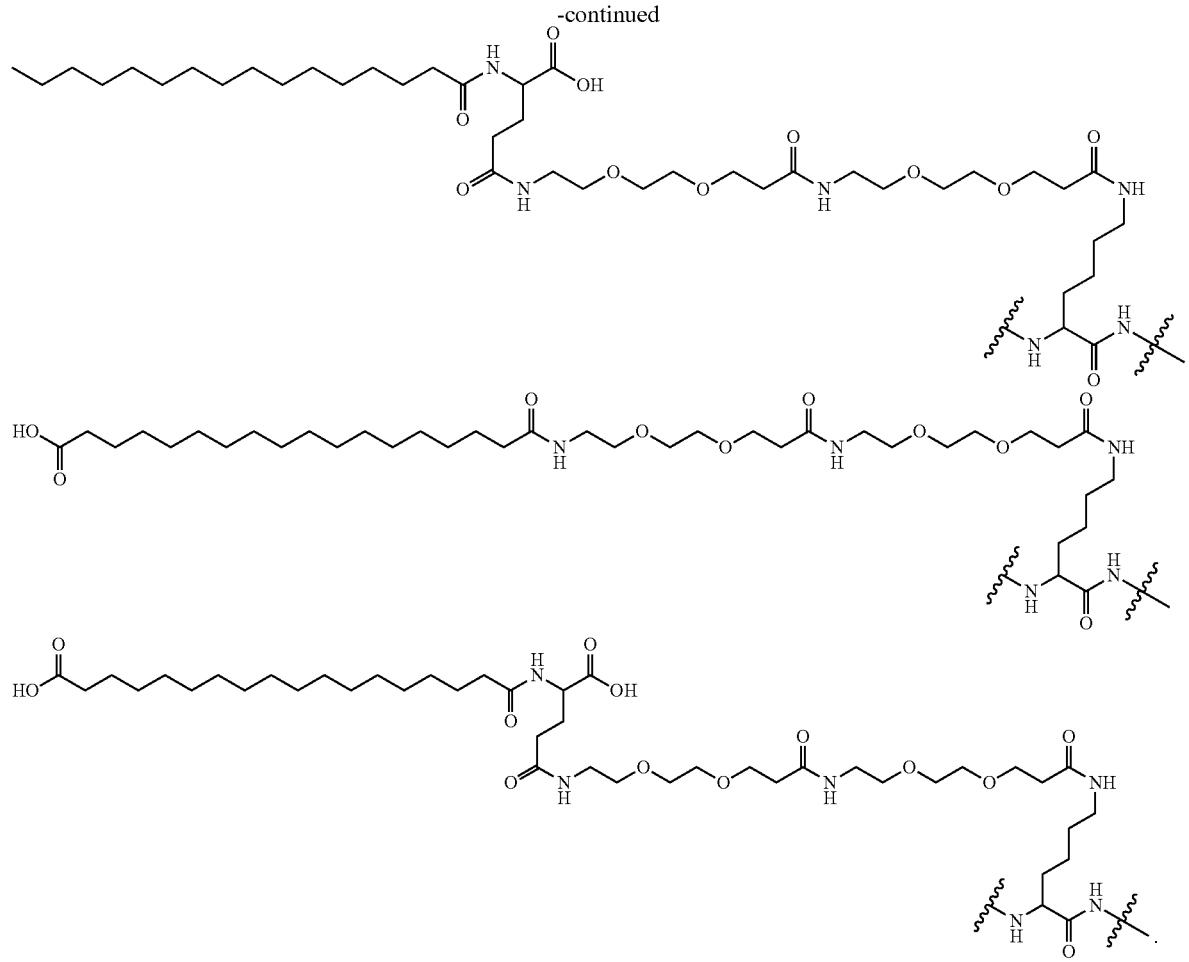
10. A pharmaceutical composition comprising the oxyntomodulin analogue of claim 3.

SEQUENCE LISTING

<160> NUMBER OF SEQ ID NOS: 29

<210> SEQ ID NO 1

```
<211> LENGTH: 29
<212> TYPE: PRT
<213> ORGANISM: Artificial Sequence
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser

<400> SEQUENCE: 1

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Arg Ala
            20                  25

<210> SEQ ID NO 2
<211> LENGTH: 29
<212> TYPE: PRT
<213> ORGANISM: Artificial Sequence
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser

<400> SEQUENCE: 2

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Arg Ala
            20                  25

<210> SEQ ID NO 3
<211> LENGTH: 39
<212> TYPE: PRT
<213> ORGANISM: Artificial Sequence
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser

<400> SEQUENCE: 3

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Asn Gly Gly Pro Ser
            20                  25                  30

Ser Gly Ala Pro Pro Ser
        35

<210> SEQ ID NO 4
<211> LENGTH: 39
<212> TYPE: PRT
<213> ORGANISM: Artificial Sequence
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser

<400> SEQUENCE: 4

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Asn Gly Gly Pro Ser
```

20                  25                  30

Ser Gly Ala Pro Pro Ser
        35

<210> SEQ ID NO 5
<211> LENGTH: 40
<212> TYPE: PRT
<213> ORGANISM: Artificial Sequence
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 5

His Ser Gln Gly Thr Phe Thr Ser Asp Lys Ser Lys Tyr Leu Asp Xaa
1               5                  10                  15

Arg Arg Ala Gln Asp Phe Val Gln Trp Leu Met Asn Thr Gly Gly Pro
            20                  25                  30

Ser Ser Gly Ala Pro Pro Ser
        35                  40

<210> SEQ ID NO 6
<211> LENGTH: 40
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: Xaa=Aib

<400> SEQUENCE: 6

His Ser Gln Gly Thr Phe Thr Ser Asp Lys Ser Lys Tyr Leu Asp Xaa
1               5                  10                  15

Arg Arg Ala Gln Asp Phe Val Gln Trp Leu Met Asn Thr Gly Gly Pro
            20                  25                  30

Ser Ser Gly Ala Pro Pro Ser
        35                  40

<210> SEQ ID NO 7
<211> LENGTH: 40
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: Xaa=Aib

<400> SEQUENCE: 7

His Ser Gln Gly Thr Phe Thr Ser Asp Lys Ser Lys Tyr Leu Asp Xaa
1               5                  10                  15

```
Arg Arg Ala Gln Asp Phe Val Gln Trp Leu Met Asn Thr Gly Gly Pro
            20                  25                  30

Ser Ser Gly Ala Pro Pro Ser
            35                  40

<210> SEQ ID NO 8
<211> LENGTH: 40
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: Xaa=Aib

<400> SEQUENCE: 8

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Ser
            35                  40

<210> SEQ ID NO 9
<211> LENGTH: 40
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser

<400> SEQUENCE: 9

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Met Asn Thr Gly Gly Pro
            20                  25                  30

Ser Ser Gly Ala Pro Pro Ser
            35                  40

<210> SEQ ID NO 10
<211> LENGTH: 40
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser

<400> SEQUENCE: 10

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Met Asn Thr Gly Gly Pro
            20                  25                  30

Ser Ser Gly Ala Pro Pro Ser
            35                  40
```

```
<210> SEQ ID NO 11
<211> LENGTH: 40
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser

<400> SEQUENCE: 11
```

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

```
<210> SEQ ID NO 12
<211> LENGTH: 40
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: Xaa=Aib

<400> SEQUENCE: 12
```

His Ser Gln Gly Thr Phe Thr Ser Asp Tyr Ser Lys Tyr Leu Asp Xaa
1               5                   10                  15

Lys Arg Ala Gln Asp Phe Val Gln Trp Leu Met Asn Thr Gly Gly Pro
            20                  25                  30

Ser Ser Gly Ala Pro Pro Pro Ser
        35                  40

```
<210> SEQ ID NO 13
<211> LENGTH: 40
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: Xaa=Aib

<400> SEQUENCE: 13
```

His Ser Gln Gly Thr Phe Thr Ser Asp Tyr Ser Lys Tyr Leu Asp Xaa
1               5                   10                  15

Lys Arg Ala Gln Asp Phe Val Gln Trp Leu Met Asn Thr Gly Gly Pro
            20                  25                  30

Ser Ser Gly Ala Pro Pro Pro Ser
        35                  40

```
<210> SEQ ID NO 14
<211> LENGTH: 40
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: Xaa=Aib

<400> SEQUENCE: 14

His Ser Gln Gly Thr Phe Thr Ser Asp Tyr Ser Lys Tyr Leu Asp Xaa
1               5                   10                  15

Lys Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 15
<211> LENGTH: 40
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: Xaa=Aib

<400> SEQUENCE: 15

His Ser Gln Gly Thr Phe Thr Ser Asp Tyr Ser Lys Lys Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 16
<211> LENGTH: 40
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: Xaa=Aib

<400> SEQUENCE: 16

His Ser Gln Gly Thr Phe Thr Ser Asp Tyr Ser Lys Lys Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40
```

```
<210> SEQ ID NO 17
<211> LENGTH: 40
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: Xaa=Aib

<400> SEQUENCE: 17

His Ser Gln Gly Thr Phe Thr Ser Asp Tyr Ser Lys Lys Leu Asp Xaa
 1               5                  10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 18
<211> LENGTH: 40
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: Xaa=Aib

<400> SEQUENCE: 18

His Ser Gln Gly Thr Phe Thr Ser Asp Tyr Ser Lys Lys Leu Asp Xaa
 1               5                  10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 19
<211> LENGTH: 39
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: Xaa=Aib

<400> SEQUENCE: 19

His Xaa Gln Gly Thr Phe Thr Ser Asp Lys Ser Lys Tyr Leu Asp Glu
 1               5                  10                  15

Arg Arg Ala Gln Asp Phe Val Gln Trp Leu Leu Asp Gly Gly Pro Ser
            20                  25                  30

Ser Gly Ala Pro Pro Pro Ser
        35
```

```
<210> SEQ ID NO 20
<211> LENGTH: 39
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: Xaa=Aib

<400> SEQUENCE: 20

His Xaa Gln Gly Thr Phe Thr Ser Asp Lys Ser Lys Tyr Leu Asp Glu
1               5                   10                  15

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 21
<211> LENGTH: 39
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: Xaa=Aib
<220> FEATURE:
<221> NAME/KEY: MISC_FEATURE
<222> LOCATION: (16)..(16)
<223> OTHER INFORMATION: Xaa=Aib

<400> SEQUENCE: 21

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 22
<211> LENGTH: 39
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: Xaa=Aib
<220> FEATURE:
<221> NAME/KEY: MISC_FEATURE
<222> LOCATION: (16)..(16)
<223> OTHER INFORMATION: Xaa=Aib

<400> SEQUENCE: 22

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 23
<211> LENGTH: 39
```

```
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser

<400> SEQUENCE: 23

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Asn Gly Gly Pro Ser
            20                  25                  30

Ser Gly Ala Pro Pro Pro Ser
        35

<210> SEQ ID NO 24
<211> LENGTH: 39
<212> TYPE: PRT
<213> ORGANISM: Artificial
<220> FEATURE:
<223> OTHER INFORMATION: Oxyntomodulin Analogue
<220> FEATURE:
<221> NAME/KEY: MISC_FEATURE
<222> LOCATION: (2)..(2)
<223> OTHER INFORMATION: D-Ser

<400> SEQUENCE: 24

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Asn Gly Gly Pro Ser
            20                  25                  30

Ser Gly Ala Pro Pro Pro Ser
        35

<210> SEQ ID NO 25
<211> LENGTH: 37
<212> TYPE: PRT
<213> ORGANISM: Homo sapiens
<220> FEATURE:
<221> NAME/KEY: PEPTIDE
<222> LOCATION: (1)..(37)
<223> OTHER INFORMATION: Parent Peptide of Oxyntomodulin

<400> SEQUENCE: 25

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Lys Asn Asn Ile Ala
        35

<210> SEQ ID NO 26
<211> LENGTH: 31
<212> TYPE: PRT
<213> ORGANISM: Homo sapiens
<220> FEATURE:
<221> NAME/KEY: PEPTIDE
<222> LOCATION: (1)..(31)
<223> OTHER INFORMATION: Glucagon-like Peptide

<400> SEQUENCE: 26

His Ala Glu Gly Thr Phe Thr Ser Asp Val Ser Ser Tyr Leu Glu Gly
1               5                   10                  15
```

Gln Ala Ala Lys Glu Phe Ile Ala Trp Leu Val Lys Gly Arg Gly
            20                  25                  30

<210> SEQ ID NO 27
<211> LENGTH: 39
<212> TYPE: PRT
<213> ORGANISM: Artificial
<220> FEATURE:
<223> OTHER INFORMATION: Exenatide

<400> SEQUENCE: 27

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 28
<211> LENGTH: 29
<212> TYPE: PRT
<213> ORGANISM: Homo sapiens
<220> FEATURE:
<221> NAME/KEY: PEPTIDE
<222> LOCATION: (1)..(29)
<223> OTHER INFORMATION: Glucagon

<400> SEQUENCE: 28

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 29
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: -OH or -NH2 at 3' end
<220> FEATURE:
<221> NAME/KEY: misc_feature
<222> LOCATION: (2)..(2)
<223> OTHER INFORMATION: Xaa can be Aib, Ser or D-Ser
<220> FEATURE:
<221> NAME/KEY: misc_feature
<222> LOCATION: (10)..(10)
<223> OTHER INFORMATION: Xaa can be Lys or Tyr
<220> FEATURE:
<221> NAME/KEY: misc_feature
<222> LOCATION: (13)..(13)
<223> OTHER INFORMATION: Xaa can be Lys or Tyr
<220> FEATURE:
<221> NAME/KEY: misc_feature
<222> LOCATION: (16)..(16)
<223> OTHER INFORMATION: Xaa can be Ser, Aib, Lys or Glu
<220> FEATURE:
<221> NAME/KEY: misc_feature
<222> LOCATION: (17)..(17)
<223> OTHER INFORMATION: Xaa can be Lys or Arg
<220> FEATURE:
<221> NAME/KEY: misc_feature
<222> LOCATION: (18)..(18)
<223> OTHER INFORMATION: Xaa can be Arg or Ala
<220> FEATURE:
<221> NAME/KEY: misc_feature
<222> LOCATION: (20)..(20)
<223> OTHER INFORMATION: Xaa can be His, Gln or Lys
<220> FEATURE:

```
<221> NAME/KEY: misc_feature
<222> LOCATION: (21)..(21)
<223> OTHER INFORMATION: Xaa can be Asp or Glu
<220> FEATURE:
<221> NAME/KEY: misc_feature
<222> LOCATION: (23)..(23)
<223> OTHER INFORMATION: Xaa can be Ile, Leu or Val
<220> FEATURE:
<221> NAME/KEY: misc_feature
<222> LOCATION: (24)..(24)
<223> OTHER INFORMATION: Xaa can be Glu or Gln
<220> FEATURE:
<221> NAME/KEY: misc_feature
<222> LOCATION: (27)..(27)
<223> OTHER INFORMATION: Xaa can be Met, Leu or is absent
<220> FEATURE:
<221> NAME/KEY: misc_feature
<222> LOCATION: (28)..(28)
<223> OTHER INFORMATION: Xaa can be Ser, Asn, Asp, Arg or is absent
<220> FEATURE:
<221> NAME/KEY: misc_feature
<222> LOCATION: (29)..(29)
<223> OTHER INFORMATION: Xaa can be Ala, Gly, Thr or is absent
<220> FEATURE:
<221> NAME/KEY: misc_feature
<222> LOCATION: (30)..(30)
<223> OTHER INFORMATION: Xaa can be Gly or is absent
<220> FEATURE:
<221> NAME/KEY: misc_feature
<222> LOCATION: (31)..(31)
<223> OTHER INFORMATION: Xaa can be Gly or is absent
<220> FEATURE:
<221> NAME/KEY: misc_feature
<222> LOCATION: (32)..(32)
<223> OTHER INFORMATION: Xaa can be Pro or is absent
<220> FEATURE:
<221> NAME/KEY: misc_feature
<222> LOCATION: (33)..(33)
<223> OTHER INFORMATION: Xaa can be Ser or is absent
<220> FEATURE:
<221> NAME/KEY: misc_feature
<222> LOCATION: (34)..(34)
<223> OTHER INFORMATION: Xaa can be Ser or is absent
<220> FEATURE:
<221> NAME/KEY: misc_feature
<222> LOCATION: (35)..(35)
<223> OTHER INFORMATION: Xaa can be Gly or is absent
<220> FEATURE:
<221> NAME/KEY: misc_feature
<222> LOCATION: (36)..(36)
<223> OTHER INFORMATION: Xaa can be Ala or is absent
<220> FEATURE:
<221> NAME/KEY: misc_feature
<222> LOCATION: (37)..(37)
<223> OTHER INFORMATION: Xaa can be Pro or is absent
<220> FEATURE:
<221> NAME/KEY: misc_feature
<222> LOCATION: (38)..(38)
<223> OTHER INFORMATION: Xaa can be Pro or is absent
<220> FEATURE:
<221> NAME/KEY: misc_feature
<222> LOCATION: (39)..(39)
<223> OTHER INFORMATION: Xaa can be Pro or is absent
<220> FEATURE:
<221> NAME/KEY: misc_feature
<222> LOCATION: (40)..(40)
<223> OTHER INFORMATION: Xaa can be Ser or is absent

<400> SEQUENCE: 29

His Xaa Gln Gly Thr Phe Thr Ser Asp Xaa Ser Lys Xaa Leu Asp Xaa
 1               5                  10                  15

Xaa Xaa Ala Xaa Xaa Phe Xaa Xaa Trp Leu Xaa Xaa Xaa Xaa Xaa Xaa
             20                  25                  30

Xaa Xaa Xaa Xaa Xaa Xaa Xaa Xaa
         35                  40
```